(12) United States Patent
Carson et al.

(10) Patent No.: US 9,359,360 B2
(45) Date of Patent: Jun. 7, 2016

(54) TLR AGONISTS

(71) Applicant: Suzanne Grimshaw, Poway, CA (US)

(72) Inventors: Dennis A. Carson, La Jolla, CA (US);
Kenji Takabayashi, Poway, CA (US);
Howard B. Cottam, Escondido, CA (US); Michael Chan, San Diego, CA (US); Christina C. N. Wu, Escondido, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 13/682,208

(22) Filed: Nov. 20, 2012

(65) Prior Publication Data

US 2013/0165455 A1   Jun. 27, 2013

Related U.S. Application Data

(63) Continuation of application No. 12/064,529, filed as application No. PCT/US2006/032371 on Aug. 21, 2006, now abandoned.

(60) Provisional application No. 60/710,337, filed on Aug. 22, 2005.

(51) Int. Cl.
*A61K 31/52* (2006.01)
*A61K 31/7076* (2006.01)
*C12P 19/40* (2006.01)
*C07D 473/16* (2006.01)
*C07D 473/34* (2006.01)
*C07D 473/18* (2006.01)
*C07D 473/24* (2006.01)

(52) U.S. Cl.
CPC ............ *C07D 473/16* (2013.01); *C07D 473/18* (2013.01); *C07D 473/24* (2013.01); *C07D 473/34* (2013.01)

(58) Field of Classification Search
None
See application file for complete search history.

(56) References Cited

U.S. PATENT DOCUMENTS

| | | |
|---|---|---|
| 4,689,338 A | 8/1987 | Gerster |
| 4,929,624 A | 5/1990 | Gerster et al. |
| 4,938,949 A | 7/1990 | Borch et al. |
| 5,037,986 A | 8/1991 | Gerster |
| 5,175,296 A | 12/1992 | Gerster |
| 5,238,944 A | 8/1993 | Wick et al. |
| 5,352,784 A | 10/1994 | Nikolaides et al. |
| 5,367,076 A | 11/1994 | Gerster |
| 5,395,937 A | 3/1995 | Nikolaides et al. |
| 5,444,065 A | 8/1995 | Nikolaides et al. |
| 5,624,677 A | 4/1997 | El-Rashidy et al. |
| 5,627,281 A | 5/1997 | Nikolaides et al. |
| 5,648,516 A | 7/1997 | Nikolaides et al. |
| 5,693,811 A | 12/1997 | Lindstrom |
| 5,736,553 A | 4/1998 | Wick et al. |
| 5,741,908 A | 4/1998 | Gerster et al. |
| 5,998,619 A | 12/1999 | Gerster et al. |
| 6,038,505 A | 3/2000 | Probst et al. |
| 6,039,969 A | 3/2000 | Tomai et al. |
| 6,083,505 A | 7/2000 | Miller et al. |
| 6,150,523 A | 11/2000 | Gerster et al. |
| 6,200,592 B1 | 3/2001 | Tomai et al. |
| 6,245,776 B1 | 6/2001 | Skwierczynski et al. |
| 6,329,381 B1 | 12/2001 | Kurimoto et al. |
| 6,333,331 B1 | 12/2001 | Moschel et al. |
| 6,372,725 B1 | 4/2002 | Zilch et al. |
| 6,437,131 B1 | 8/2002 | Gerster et al. |
| 6,486,168 B1 | 11/2002 | Skwierczynski et al. |
| 6,534,654 B2 | 3/2003 | Gerster et al. |
| 6,552,192 B1 | 4/2003 | Hanus et al. |
| 6,610,319 B2 | 8/2003 | Tomai et al. |
| 6,613,902 B2 | 9/2003 | Gerster et al. |
| 6,624,305 B2 | 9/2003 | Gerster |
| 6,696,076 B2 | 2/2004 | Tomai et al. |
| 6,706,728 B2 | 3/2004 | Hedenstrom et al. |
| 6,716,840 B2 | 4/2004 | Chu et al. |
| 6,733,764 B2 | 5/2004 | Martin |
| 6,734,187 B1 | 5/2004 | Tanaka et al. |
| 6,897,314 B2 | 5/2005 | Gerster et al. |
| 6,960,582 B2 | 11/2005 | Boyce et al. |
| 7,001,609 B1 | 2/2006 | Matson et al. |
| 7,157,465 B2 | 1/2007 | Isobe et al. |
| 7,189,727 B2 | 3/2007 | Boyce |
| 7,238,700 B2 | 7/2007 | Palle et al. |
| 7,241,890 B2 | 7/2007 | Kasibhatla et al. |
| 7,521,454 B2 | 4/2009 | Isobe et al. |
| 7,576,068 B2 | 8/2009 | Averett |

(Continued)

FOREIGN PATENT DOCUMENTS

| | | |
|---|---|---|
| AU | 2007257423 | 5/2012 |
| EP | 0145340 A2 | 6/1985 |

(Continued)

OTHER PUBLICATIONS

Lippard, Stephen J. The Art of Chemistry. Nature 2002. 416, p. 587.*

(Continued)

*Primary Examiner* — Kevin Hill
*Assistant Examiner* — Arthur S Leonard
(74) *Attorney, Agent, or Firm* — Schwegman Lundberg & Woessner, P.A.

(57) ABSTRACT

The present invention provides for TLR agonist conjugates (compounds) and compositions, as well as methods of using them. The compounds of the invention are broad-spectrum, long-lasting, and non-toxic combination of synthetic immunostimulatory agents, which are useful for activating the immune system of a mammal, preferably a human and can help direct the pharmacophore to the receptor within the endosomes of target cells and enhance the signal transduction induced by the pharmacophore.

13 Claims, 13 Drawing Sheets

(56) References Cited

U.S. PATENT DOCUMENTS

| | | |
|---|---|---|
| 7,754,728 B2 | 7/2010 | Isobe et al. |
| 7,968,544 B2 | 6/2011 | Graupe et al. |
| 8,211,863 B2 | 7/2012 | Averett |
| 8,357,374 B2 | 1/2013 | Carson et al. |
| 8,729,088 B2 | 5/2014 | Carson et al. |
| 8,790,655 B2 | 7/2014 | Carson |
| 8,846,697 B2 | 9/2014 | Carson et al. |
| 2002/0127224 A1 | 9/2002 | Chen |
| 2002/0193595 A1 | 12/2002 | Chu et al. |
| 2003/0187261 A1 | 10/2003 | Havlicek et al. |
| 2003/0191086 A1 | 10/2003 | Hanus et al. |
| 2004/0023211 A1 | 2/2004 | Groen et al. |
| 2004/0091491 A1* | 5/2004 | Kedl et al. .................. 424/178.1 |
| 2004/0132748 A1 | 7/2004 | Isobe et al. |
| 2004/0209899 A1 | 10/2004 | Palle et al. |
| 2004/0248895 A1 | 12/2004 | Chu et al. |
| 2004/0265351 A1 | 12/2004 | Miller et al. |
| 2005/0004144 A1 | 1/2005 | Carson et al. |
| 2005/0038027 A1 | 2/2005 | Boyce |
| 2005/0049263 A1 | 3/2005 | Kasibhatla et al. |
| 2005/0054590 A1 | 3/2005 | Averett |
| 2005/0059613 A1 | 3/2005 | Memarzadeh et al. |
| 2005/0266067 A1 | 12/2005 | Sengupta et al. |
| 2006/0052403 A1 | 3/2006 | Isobe et al. |
| 2006/0110746 A1 | 5/2006 | Andre et al. |
| 2007/0037832 A1 | 2/2007 | Isobe et al. |
| 2007/0087009 A1 | 4/2007 | Burdin |
| 2007/0100146 A1 | 5/2007 | Dzwiniel |
| 2007/0161582 A1 | 7/2007 | Mijikovic et al. |
| 2007/0173483 A1 | 7/2007 | Kasibhatla et al. |
| 2007/0190071 A1 | 8/2007 | Kurimoto et al. |
| 2007/0292418 A1 | 12/2007 | Fields et al. |
| 2008/0008682 A1 | 1/2008 | Chong et al. |
| 2008/0125446 A1 | 5/2008 | Kasibhatla et al. |
| 2008/0214580 A1 | 9/2008 | Neagu et al. |
| 2009/0047249 A1 | 2/2009 | Graupe et al. |
| 2009/0069289 A1 | 3/2009 | Neagu et al. |
| 2009/0099212 A1 | 4/2009 | Zablocki et al. |
| 2009/0105212 A1 | 4/2009 | Isobe et al. |
| 2009/0118263 A1 | 5/2009 | Hashimoto et al. |
| 2009/0202484 A1 | 8/2009 | Chong et al. |
| 2009/0202626 A1 | 8/2009 | Carson et al. |
| 2009/0324551 A1 | 12/2009 | Carson et al. |
| 2010/0210598 A1 | 8/2010 | Carson et al. |
| 2011/0098248 A1 | 4/2011 | Halcomb et al. |
| 2011/0098294 A1 | 4/2011 | Carson et al. |
| 2011/0319442 A1 | 12/2011 | Leoni et al. |
| 2012/0003298 A1 | 1/2012 | Barberis et al. |
| 2012/0009247 A1 | 1/2012 | Maj et al. |
| 2012/0083473 A1 | 4/2012 | Holldack et al. |
| 2012/0148660 A1 | 6/2012 | Carson et al. |
| 2012/0177681 A1 | 7/2012 | Singh et al. |
| 2013/0156807 A1 | 6/2013 | Carson et al. |
| 2013/0190494 A1 | 7/2013 | Carson et al. |
| 2014/0302120 A1 | 10/2014 | Carson et al. |

FOREIGN PATENT DOCUMENTS

| | | | |
|---|---|---|---|
| EP | 0310950 A1 | 4/1989 | |
| EP | 0389302 A1 | 9/1990 | |
| EP | 0394026 A1 | 10/1990 | |
| EP | 0553202 A1 | 8/1993 | |
| EP | 0575549 A1 | 12/1993 | |
| EP | 0636031 A1 | 2/1995 | |
| EP | 0681570 A1 | 11/1995 | |
| EP | 0708773 A1 | 5/1996 | |
| EP | 0912564 A1 | 5/1999 | |
| EP | 0912565 A1 | 5/1999 | |
| EP | 0938315 A1 | 9/1999 | |
| EP | 1035123 * | 9/2000 | .......... C07D 473/16 |
| EP | 1035123 A1 | 9/2000 | |
| EP | 1035123 B1 | 8/2003 | |
| EP | 1386923 A1 | 2/2004 | |
| EP | 1550662 * | 6/2005 | .......... C07D 473/18 |
| EP | 1550662 A1 | 7/2005 | |
| EP | 1939202 A1 | 7/2008 | |
| EP | 2396328 | 12/2011 | |
| HK | 1138767 B | 5/2014 | |
| JP | 11193282 A | 7/1999 | |
| JP | 2004137157 A | 5/2004 | |
| JP | 2005046160 A | 2/2005 | |
| JP | 2005505504 A | 2/2005 | |
| JP | 200589334 A | 4/2005 | |
| JP | 2005089334 A | 4/2005 | |
| JP | 2007-504232 A | 3/2007 | |
| JP | 2009-504803 A | 2/2009 | |
| JP | 2009-510096 A | 3/2009 | |
| JP | 2012517428 A | 8/2012 | |
| JP | 2013525431 A | 6/2013 | |
| WO | WO-9215581 A1 | 9/1992 | |
| WO | WO-9320847 A1 | 10/1993 | |
| WO | WO-9817279 A1 | 4/1998 | |
| WO | WO-9848805 A1 | 11/1998 | |
| WO | WO-9928321 A1 | 6/1999 | |
| WO | WO-0043394 A1 | 7/2000 | |
| WO | WO-0144259 A1 | 6/2001 | |
| WO | WO-0144260 A2 | 6/2001 | |
| WO | WO-01/49688 A1 | 7/2001 | |
| WO | WO-0224225 A1 | 3/2002 | |
| WO | WO-03077944 A1 | 9/2003 | |
| WO | WO-2004029054 A1 | 4/2004 | |
| WO | WO-2005025583 A2 | 3/2005 | |
| WO | WO-2005060966 A1 | 7/2005 | |
| WO | WO-2005092892 A1 | 10/2005 | |
| WO | WO-2006062945 A2 | 6/2006 | |
| WO | WO-2006100226 A1 | 9/2006 | |
| WO | WO-2007/034817 A1 | 3/2007 | |
| WO | WO-2007/034917 A1 | 3/2007 | |
| WO | WO-2007024707 A2 | 3/2007 | |
| WO | WO-2007024707 A3 | 3/2007 | |
| WO | WO-2007/038720 A2 | 4/2007 | |
| WO | WO-2007142755 A2 | 12/2007 | |
| WO | WO-2007142755 A3 | 12/2007 | |
| WO | WO-2008115319 A2 | 9/2008 | |
| WO | WO-2008115319 A3 | 9/2008 | |
| WO | WO-2009005687 A1 | 1/2009 | |
| WO | WO-2009099650 A2 | 8/2009 | |
| WO | WO-2009099650 A3 | 8/2009 | |
| WO | WO-2009099650 A4 | 8/2009 | |
| WO | WO-2010093436 A2 | 8/2010 | |
| WO | WO-2011139348 A2 | 11/2011 | |

OTHER PUBLICATIONS

Julien ("Chapter 2: Pharmacodynamics: How Drugs Act", A Primer of Drug Action (Ninth Edition); Worth Publishers, 2001:37-57.*
Brown, Gordon. Dectin-1: a signalling non-TLR pattern-recognition receptor. Nature Reviews Immunology 2006. 6: 33-43.*
Interchim Inc., Isolation/Modification/Labeling Product Sheet, Jan. 15, 2000, p. 1-23.*
Horner et al., Optimized conjugation ratios lead to allergen immunostimulatory oligodeoxynucleotide conjugates with retained immunogenicity and minimal anaphylactogenicity. J Allergy Clin Immunol, 2002;110:413-20.*
"8H-Purin-8-one, 6-amino-2-(butylthio)-7,9-dihydro-9-(phenylmethyl)-", CAS Registry No. 226906-70-3.
"8H-Purin-8-one, 6-amino-2-(cyclohexylthio)-7,9-dihydro-9-(phenylmethyl)-", CAS Registry No. 226906-76-9.
"8H-Purin-8-one, 6-amino-2-(ethylthio)-7,9-dihydro-9-(phenylmethyl)-", CAS Registry No. 226906-67-8.
"8H-Purin-8-one, 6-amino-7,9-dihydro-2-(methylthio)-9-(phenylmethyl)-", CAS Registry No. 226906-66-7.
"8H-Purin-8-one, 6-amino-7,9-dihydro-2-(pentylthio)-9-(phenylmethyl)-", CAS Registry No. 226906-73-6.
"8H-Purin-8-one, 6-amino-7,9-dihydro-2-[(1-methylethyl)thio]-9-(phenylmethyl)-", CAS Registry No. 226906-69-0.
"8H-Purin-8-one, 6-amino-7,9-dihydro-2-[(1-methylpropyl)thio]-9-(phenylmethyl)-", CAS Registry No. 226906-72-5.
"8H-Purin-8-one, 6-amino-7,9-dihydro-2-[(2-methylbutyl)thio]-9-(phenylmethyl)-", CAS Registry No. 226906-75-8.

(56) References Cited

OTHER PUBLICATIONS

"8H-Purin-8-one, 6-amino-7,9-dihydro-2-[(2-methylpropyl)thio]-9-(phenylmethyl)-", CAS Registry No. 226906-71-4.
"8H-Purin-8-one, 6-amino-7,9-dihydro-2-[(3-methylbutyl)thio]-9-(phenylmethyl)-", CAS Registry No. 226906-74-7.
"8H-Purin-8-one, 6-amino-7,9-dihydro-9-(phenylmethyl)-2-(phenylthio)-", CAS Registry No. 226906-77-0.
"8H-Purin-8-one, 6-amino-7,9-dihydro-9-(phenylmethyl)-2-(propylthio)-", CAS Registry No. 226906-68-9.
"U.S. Appl. No. 12/027,960, Non Final Office Action mailed Apr. 10, 2012", 16 pgs.
"U.S. Appl. No. 12/027,960, Notice of Allowance mailed Aug. 1, 2012", 11 pgs.
"U.S. Appl. No. 12/027,960, Preliminary Amendment mailed Dec. 8, 2010", 21 pgs.
"U.S. Appl. No. 12/027,960, Response filed Jul. 10, 2012 to Non Final Office Action mailed Apr. 10, 2012", 8 pgs.
"U.S. Appl. No. 12/027,960, Response filed Oct. 24, 2011 to Restriction Requirement mailed Sep. 23, 2011", 21 pgs.
"U.S. Appl. No. 12/027,960, Response to Rule 312 Communication mailed Nov. 14, 2012", 2 pgs.
"U.S. Appl. No. 12/027,960, Restriction Requirement mailed Sep. 23, 2011", 9 pgs.
"U.S. Appl. No. 12/064,529 , Response filed Jul. 9, 2012 to Non Final Office Action mailed Apr. 9, 2012", 11 pgs.
"U.S. Appl. No. 12/064,529, Final Office Action mailed Sep. 20, 2012", 14 pgs.
"U.S. Appl. No. 12/064,529, Non Final Office Action mailed Apr. 9, 2012", 15 pgs.
"U.S. Appl. No. 12/064,529, Response filed Oct. 24, 2011 to Restriction Requirement mailed Aug. 24, 2011", 9 pgs.
"U.S. Appl. No. 12/064,529, Restriction Requirement mailed Aug. 24, 2011", 9 pgs.
"U.S. Appl. No. 12/302,738, Restriction Requirement mailed Oct. 19, 2012", 7 pgs.
"U.S. Appl. No. 12/367,172 , Response filed Aug. 13, 2012 to Final Office Action mailed Apr. 13, 2012", 9 pgs.
"U.S. Appl. No. 12/367,172, Final Office Action mailed Jan. 18, 2012", 15 pgs.
"U.S. Appl. No. 12/367,172, Final Office Action mailed Apr. 13, 2012", 21 pgs.
"U.S. Appl. No. 12/367,172, Non Final Office Action mailed May 27, 2011", 20 pgs.
"U.S. Appl. No. 12/367,172, Response filed Mar. 8, 2011 to Restriction Requirement mailed Dec. 8, 2010", 11 pgs.
"U.S. Appl. No. 12/367,172, Response filed Nov. 16, 2011 to Non Final Office Action mailed May 27, 2011", 6 pgs.
"U.S. Appl. No. 12/367,172, Restriction Requirement mailed Dec. 8, 2010", 6 pgs.
"U.S. Appl. No. 12/704,343, Non Final Office Action mailed Jul. 16, 2012", 14 pgs.
"U.S. Appl. No. 12/704,343, Response filed Jul. 5, 2012 to Restriction Requirement mailed May 7, 2012", 7 pgs.
"U.S. Appl. No. 12/704,343, Response filed Oct. 16, 2 to Non Final Office Action mailed Jul. 16, 2012", 12 pgs.
"U.S. Appl. No. 12/704,343, Restriction Requirement mailed May 7, 2012", 7 pgs.
"Australia Application Serial No. 2008227128, First Examiner Report mailed Jul. 6, 2012", 2 pgs.
"Australian Application Serial No. 2006283524, Office Action mailed Mar. 27, 2008", 1 pg.
"Australian Application Serial No. 2006283524, Office Action mailed Aug. 3, 2011", 4 pgs.
"Australian Application Serial No. 2006283524, Preliminary Amendment mailed Mar. 3, 2008", 18 pgs.
"Australian Application Serial No. 2006283524, Response filed May 19, 2008 to Office Action mailed Mar. 27, 2008", 10 pgs.
"Australian Application Serial No. 2006283524, Response filed Aug. 2, 2012 to Examiner Report mailed Aug. 3, 2011", 34 pgs.
"Australian Application Serial No. 2007257423, Examiner Report mailed Jun. 6, 2011", 2 pgs.
"Australian Application Serial No. 2007257423, First Examiner Report mailed Sep. 22, 2010", 4 Pgs.
"Australian Application Serial No. 2007257423, Office Action mailed Oct. 20, 2011", 2 pgs.
"Australian Application Serial No. 2007257423, Response filed May 31, 2011 to First Examiner Report mailed Sep. 22, 2010", 16 pgs.
"Australian Application Serial No. 2007257423, Response filed Sep. 13, 2011 to Examination Report mailed Jun. 6, 2011", 12 pgs.
"Australian Application Serial No. 2007257423, Response filed Dec. 19, 2011 to Office Action mailed Oct. 20, 2011", 5 pgs.
"Australian Application Serial No. 2008227128, Preliminary Amendment filed Sep. 7, 2009", 45 pgs.
"Brazilian Application Serial No. PI 0807196-9, Amendment filed Mar. 2, 2011", 13 pgs.
"Canadian Application Serial No. 2,620,182, Office Action mailed Aug. 24, 2012", 5 pgs.
"Canadian Application Serial No. 2,653,941, Office Action May 10, 2011", 3 pgs.
"Canadian Application Serial No. 2,653,941, Office Action mailed Feb. 8, 2012", 2 pgs.
"Canadian Application Serial No. 2,653,941, Office Action mailed Aug. 23, 2010", 5 pgs.
"Canadian Application Serial No. 2,653,941, Response filed Feb. 23, 2011 to Office Action mailed Aug. 23, 2010", 20 pgs.
"Canadian Application Serial No. 2,653,941, Response filed Aug. 2, 2012 to Office Action mailed Feb. 8, 2012", 7 pgs.
"Canadian Application Serial No. 2,653,941, Response filed Nov. 9, 2011 to Office Action mailed May 10, 2011", 15 pgs.
"Canadian Application Serial No. 2,677,733, Voluntary Amendment filed Aug. 7, 2009", 45 pgs.
"Chinese Application Serial No. 200680038761.X, Office Action mailed Mar. 22, 2012", 9 pgs.
"Chinese Application Serial No. 200680038761.X, Office Action mailed Apr. 14, 2010", with English translation, 9 pgs.
"Chinese Application Serial No. 200680038761.X, Office Action mailed Jun. 23, 2011", (w/ English Translation), 9 pgs.
"Chinese Application Serial No. 200680038761.X, Office Action Response Filed Oct. 29, 2010", with English translation of amended claims, 22 pgs.
"Chinese Application Serial No. 200680038761.X, Response filed Sep. 7, 2011 to Office Action mailed Jun. 23, 2011", (w/ English Translation of Amended Claims), 19 pgs.
"Chinese Application Serial No. 200680038761.X, Response filed Jul. 6, 2012 to Action mailed Mar. 22, 2012", 9 pgs.
"Chinese Application Serial No. 200880011525.8, Office Action mailed Jan. 30, 2012", English Translation Only, 6 pgs.
"Chinese Application Serial No. 200880011525.8, Office Action mailed Jul. 5, 2012", 14 pgs.
"Chinese Application Serial No. 200880011525.8, Office Action mailed Oct. 16, 2012", 13 pgs.
"Chinese Application Serial No. 200880011525.8, Response filed Jun. 13, 2012 to Office Action mailed Jan. 30, 2012", 14 pgs.
"Chinese Application Serial No. 200880011525.8, Response filed Sep. 20, 2012 to Office action Mailed Jul. 5, 2012", 12 pgs.
"Chinese Application Serial No. 200880011525.8, Voluntary Amendment filed Dec. 2, 2010", (w/ English Translation of Claims), 12 pgs.
"Chinese Application Serial No. 200980112411.7, Response filed Aug. 15, 2012 to Office Action mailed Feb. 2, 2012", (w/ English Translation of Amended Claims), 70 pgs.
"Chinese Application Serial No. 200980112411.7, Voluntary Amendment filed Jan. 31, 2011", (w/ English Translation of Claims), 74 pgs.
"Chinese Application Serial No. 200980112411.7, Office Action Mailed Feb. 2, 2012", w/ English Translation, 9 pgs.
"Eurasian Application Serial No. 201001264, Office Action mailed Sep. 12, 2012", 1 pg.
"Eurasian Application Serial No. 200901078, Office Action mailed Apr. 2, 2012", w/English Translation, 3 pgs.
"Eurasian Application Serial No. 200901078, Office Action mailed May 26, 2011", 5 pgs.

(56) References Cited

OTHER PUBLICATIONS

"Eurasian Application Serial No. 200901078, Office Action mailed Sep. 21, 2011", (w/ English Translation), 4 pgs.
"Eurasian Application Serial No. 200901078, Office Action mailed Sep. 18, 2012", 4 pgs.
"Eurasian Application Serial No. 200901078, Response filed Sep. 13, 2011", 13 pgs.
"Eurasian Patent Application Serial No. 200901078, Response filed Mar. 21, 2012 to Office Action mailed Sep. 21, 2011", 8 pgs.
"Eurasian Patent Application Serial No. 200901078, Response filed Aug. 2, 2012 to Office Action mailed Apr. 2, 2012", 2 pgs.
"European Application Serial No. 12004181.9, Extended EP Search Report mailed Sep. 13, 2012", 8 pgs.
"European Application Serial No. 06813535.9, Extended Search Report mailed Oct. 24, 2011", 6 pgs.
"European Application Serial No. 06813535.9, Response filed May 14, 2012 to Extended Search Report mailed Oct. 24, 2011", 18 pgs.
"European Application Serial No. 06813535.9, Voluntary Amendment filed Apr. 22, 2008", 9 pgs.
"European Application Serial No. 07755916.9, Office Action mailed Nov. 11, 2011", 1 pg.
"European Application Serial No. 07755916.9, Response filed May 18, 2012 to Extended Search Report mailed Oct. 25, 2011", 11 pgs.
"European Application Serial No. 07755916.9, Supplemental Search Report mailed Oct. 25, 2011", 9 pgs.
"European Application Serial No. 08799591.6, Office Action mailed May 21, 2012", 4 pgs.
"European Application Serial No. 08799591.6, Office Action mailed Jun. 4, 2010", 4 pgs.
"European Application Serial No. 08799591.6, Office Action Response Dated Sep. 20, 2012", 31 Pgs.
"European Application Serial No. 08799591.6, Response filed Nov. 22, 2011 to Office Action mailed May 17, 2011", 26 pgs.
"European Application Serial No. 08799591.6, Response filed Dec. 2, 2010 to Office Action mailed Jun. 4, 2010", 20 pgs.
"European Application Serial No. 09709019.5, Extended European Search Report mailed Feb. 15, 2011", 8 pgs.
"European Application Serial No. 08799591.6, Examination Notification Art. 94(3) mailed May 17, 2011", 5 pgs.
"I. Pharmaceutical Importance of Crystallin Hydrates", [online]. [retrieved on May 30, 2008]. Retrieved from the Internet: <URL: http://www.netlibrary.com/nlreader.dll?bookid=12783 &filename=Page_126. html>, (2008), 126-127.
"International Application Serial No. PCT/US06/32371, International Search Report mailed Jul. 23, 2007", 3 pgs.
"International Application Serial No. PCT/US06/32371, Written Opinion mailed Jul. 23, 2007", 6 pgs.
"International Application Serial No. PCT/US2007/009840, International Preliminary Report on Patentability mailed Dec. 18, 2008", 9 pgs.
"International Application Serial No. PCT/US2008/001631, International Preliminary Examination Report mailed Aug. 20, 2009", 12 pgs.
"International Application Serial No. PCT/US2008/001631, International Search Report mailed Jan. 21, 2009", 6 pgs.
"International Application Serial No. PCT/US2008/001631, Written Opinion mailed Jan. 21, 2009", 9 pgs.
"International Application Serial No. PCT/US2009/000771, International Search Report mailed Aug. 28, 2009", 4 pgs.
"International Application Serial No. PCT/US2009/000771, Written Opinion mailed Aug. 28, 2009", 5 pgs.
"International Application Serial No. PCT/US2010/000369, International Preliminary Report on Patentability dated Jun. 28, 2011", 13 pgs.
"International Application Serial No. PCT/US2010/000369, International Search Report mailed Sep. 21, 2010", 6 pgs.
"International Application Serial No. PCT/US2010/000369, Partial International Search Report mailed Jul. 5, 2010", 6 pgs.
"International Application Serial No. PCT/US2010/000369, Written Opinion mailed Feb. 11, 2010", 9 pgs.
"International Application Serial No. PCT/US2010/000369, Written Opinion mailed Sep. 21, 2010", 9 pgs.
"Israeli Application Serial No. 200240, Examiner Report mailed Aug. 28, 2012", 4 pgs.
"Japanese Application Serial No. 2008-528017, Office Action mailed May 22, 2012", 7 pgs.
"Japanese Application Serial No. 2008-528017, Preliminary Amendment filed Aug. 12, 2009", 26 pgs.
"Japanese Application Serial No. 2009-549102, Office Action mailed Oct. 12, 2012", 3 pgs.
"Japanese Application Serial No. 2009-549102, Voluntary Amendment filed Feb. 7, 2011", (w/ English Translation of Amended Claims), 24 pgs.
"Japanese Application No. 2010-545884, Voluntary Amendment filed Oct. 7, 2010", 65 pgs.
"Mexican Application Serial No. MX/a/2010/008697, Office Action mailed Nov. 28, 2011", 4 pgs.
"Mexican Application Serial No. MX/a/2010/008697, Response filed Jul. 10, 2012 to Office Action mailed May 4, 2012", 5 pgs.
"Mexican Application Serial No. MX/a/2010/8697, Office Action mailed May 10, 2012", (English Translation), 3 pgs.
"Mexican Appplication Serial No. MX/a/2010/008697 , Office Action Response Filed Mar. 28, 2012", 22 pgs.
"Singapore Applicaiton Serial No. 201005638-0, Office Action mailed Jun. 27, 2012", 7 pgs.
"Singapore Application Serial No. 201005638-0, Response filed Aug. 22, 2012 to Office Action mailed Jun. 27, 2012", 2 pgs.
"Singapore Application Serial No. 201005638-0, Office Action mailed Nov. 9, 2011", 16 pgs.
"Singapore Application Serial No. 201005638-0, Search Report mailed Oct. 27, 2011", 7 pgs.
"Singapore Application Serial No. 201005638-0, Written Opinion mailed Oct. 27, 2011", 8 pgs.
"Singapore Application Serial No. 201005638-0, Office Action Response filed Mar. 29, 2012 to Office Action mailed Nov. 9, 2011", (English Translation), 91 pgs.
Baenziger, S., et al., "Triggering TLR7 in mice induces immune activation and lymphoid system disruption, resembling HIV-mediated pathology", Blood, 113(2), (Jan. 8, 2009), 377-388.
Bryan, G. T., et al., "Interferon (IFN) and IFN Inducers Protect Mouse Bladder Urothelium Against Carcinogenicity by FANFT", Journal of Cancer Research and Clinical Oncology, 116(Suppl. Part 1), (Abstract A3.106.36), (15th International Cancer Congress, Hamburg, Aug. 16-22, 1990), (1990), p. 308.
Carson, D. A., et al., "TLR Agonists", U.S. Appl. No. 60/710,337, filed Aug. 22, 2005, 52 pgs.
Chan, M., et al., "Synthesis and immunological characterization of toll-like receptor 7 agonistic conjugates", Bioconjug Chem., 20(6), (Jun. 2009), 1194-200.
Colombo, R., et al., "Combination of intravesical chemotherapy and hyperthermia for the treatment of superficial bladder cancer: preliminary clinical experience", Crit Rev Oncol Hematol., 47(2), (Aug. 2003), 127-39.
Dolan, M. E, et al., "Metabolism of O6-benzylguanine, an inactivator of O6-alkylguanine-DNA alkyltransferase.", Cancer Res., 54(19), (Oct. 1, 1994), 5123-30.
Hayashi, T., et al., "Mast cell-dependent anorexia and hypothermia induced by mucosal activation of Toll-like receptor 7", Am J Physiol Regul Integr Comp Physiol., 295(1), (2008), R123-32.
Jin, "", Bioorganic & Medicianl Chemistry Letter, vol. 16, No. 17, (2006), 4559-4563.
Jin, G., et al., "Synthesis and immunostimulatory activity of 8-substituted amino 9-benzyladenines as potent Toll-like receptor 7 agonists.", Bioorg Med Chem Lett., 16(17), (Sep. 1, 2006), 4559-63.
Kobayashi, H., et al., "Prepriming: a novel approach to DNA-based vaccination and immunomodulation", Springer Seminars in Immunopathology, 22(Nos. 1-2), (2000), 85-96.
Kulikov, V. I, et al., "Lipid derivatives of prostaglandins and nonsteroidal antiinflammatory drugs (a review)", Pharmaceutical Chemistry Journal, 31(4), (1997), 173-177.
Kurimoto, A., et al., "Synthesis and structure-activity relationships of 2-amino-8-hydroxyadenines as orally active interferon inducing agents", Bioorg Med Chem., 11(24), (Dec. 1, 2003), 5501-8.

(56) References Cited

OTHER PUBLICATIONS

Lee, J., et al., "Molecular basis for the immunostimulatory activity of guanine nucleoside analogs: Activation of Toll-like receptor 7", Proc. Natl. Acad. Sci., 100(11), (2003), 6646-6651.
Liu, H., et al., "Tumour growth inhibition by an imidazoquinoline is associated with c-Myc down-regulation in urothelial cell carcinoma", BJU International, 101(7), (Apr. 2008), 894-901.
Mayer, R., et al., "A randomized controlled trial of intravesical bacillus calmette-guerin for treatment refractory interstitial cystitis", Journal of Urology, 173(4), (Apr. 2005), 1186-1191.
Metzler, David E, "Biosynthesis of triglycerides and phospholipids", Biochemistry: The Chemical Reactions of Living Cells, (1977), 3 pgs.
Miller, R L, et al., "Imiquimod applied topically: a novel immune response modifier and new class of drug", Int J Immunopharmacol., 21(1), (Jan. 1999), 1-14.
Mosmann, T. R., et al., "TH1 and TH2 cells: different patterns of lymphokine secretion lead to different functional properties", Annual Review Immunology, 7, (1989), 145-173.
Rohn, S., et al., "Antioxidant activity of protein-bound quercetin", J Agric Food Chem., 52(15), (Jul. 28, 2004), 4725-9.
Schon, M., et al., "Tumor-Selective Induction of Apoptosis and the Small-Molecule Immune Response Modifier Imiquimod", J Natl Cancer Inst, 95(15), (2003), 1138-1149.
Sidky, Y. A., et al., "Curative effectiveness of the interferon inducing imiquimod as a signal agent in mouse bladder tumors", Proceedings, Eighty-Fourth Meeting of the American Association for Cancer Research, vol. 34, (Abstract 2789) (May 19-22, 1993, Orlando, FL), (Mar. 1993), p. 467.
Sidky, Y. A, et al., "Effects of Treatment with an Oral Interferon Inducer, Imidazoquinolinamine (R-837), on the Growth of Mouse Bladder Carcinoma FCB", Journal of Interferon Research, 10(Supp 1), (Abstract II6-12) (Annual Meeting of the ISIR, San Francisco, CA, Nov. 14-18, 1990), (Nov. 1990), S123.
Sidky, Y. A., et al., "Effects of treatment with the oral interferon inducer, R-837, on the growth of mouse colon carcinoma, MC-26", Proceedings, 81st Annual Meeting of the American Association for Cancer Research, vol. 31, (Abstract 2574), (Mar. 1990), p. 433.
Sidky, Y. A, et al., "Inhibition of murine tumor growth by an interferon-inducing imidazoquinolinamine", Cancer Research, 52(13), (Jul. 1, 1992), 3528-33.
Sidky, Y. A., et al., "Inhibition of tumor-induced angiogenesis by the interferon inducer Imiquimod", Proceedings, Eighty-Third Annual Meeting of the American Association of Cancer Research, vol. 33, (Abstract 458) (May 20-23, 1992, San Diego, CA), (Mar. 1992), p. 77.
Simons, M. P., et al., "Identification of the Mycobacterial Subcomponents Involved in the Release of Tumor Necrosis Factor Related Apoptosis—Including Ligand from Human Neutrophills Infection and Immunity", Infection and Immunity, 75(3), (2007), 1265-1271.
Simons, M. P., et al., "Identification of the Mycobacterial Subcomponents Involved in the Release of Tumor Necrosis Factor-Related Apoptosis-Inducing Ligand from Human Neutrophils", Infection and Immunity, 75(3), (2007), 1265-1271.
Smith, E. B, et al., "Antitumor effects of imidazoquinolines in urothelial cell carcinoma of the bladder", J Urol., 177(6), (May 2007), 2347-51.
Smith, E. B., et al., "Antitumor Effects of Imidazoquinolines in Urothelial Cell Carcinoma of the Bladder", The Journal of Urology, 177(6), (Abstract Only), (2007), 3 pgs.
Smith, E. B., et al., "Effects of Imiquimod, a toll-like receptor-7 agonist, on cell proliferation and cytokine production in bladder cancer in vitro and in vivo", Journal of Urology, 173(4, Suppl. S), (Apr. 2005), p. 158.
Smith, Eric B., et al., "Antitumor Effects of Imidazoquinolines in Urothelial Cell Carcinoma of the Bladder", The Journal of Urology, 177(6), (Jun. 2007), 2347-2351.
Spohn, R., et al., "Synthetic lipopeptide adjuvants and Toll-like receptor 2-structure-activity relationships", Vaccine, 22(19), (Jun. 23, 2004), 2494-9.
Veronese, F. M., et al., "The impact of PEGylation on biological therapies", BioDrugs, 22(5), (2008), 315-329.
Wille-Reece, U., et al., "HIV Gag protein conjugated to a Toll-like receptor 7/8 agonist improves the magnitude and quality of Th1 and CD8+ T cell responses in nonhuman primates", Proc. Natl. Acad. Sci. USA, 102(42), (Oct. 18, 2005), 15190-15194.
Wille-Reece, Ulrike, "", PNAS, vol. 102, No. 42, (2005), 15190-15194.
Wu, C., et al., "Immunotherapeutic activity of a conjugate of a Toll-like receptor 7 ligand", Proc. Natl. Acad. Sci. USA, 104(10), (2007), 3990-3995.
Wu, Christina C N, "", PNAS, vol. 104, No. 10, (Mar. 6, 2007), 3990-3995.
Yang, Victor C., et al., "Bioconjugates for Effective Drug Targeting", Advanced Drug Delivery Reviews 55 (2003), (2002), 169-170.
Zaks, K, et al., "Efficient immunization and cross-priming by vaccine adjuvants containing TLR3 or TLR9 agonist complexed to cationic Liposomes", Journal of Immunology, 176(12), (Jun. 15, 2006), 7335-7345.
Zaks, Karen, "", The Journal of Immunology, vol. 176, No. 12, (2006), 7335-7345.
"U.S. Appl. No. 12/027,960, Amendment Under 37 C.F.R. Sec. 1.312 filed Nov. 1, 2012", 7 pgs.
"U.S. Appl. No. 12/064,529, Preliminary Amendment filed Feb. 22, 2008", 11 pgs.
"U.S. Appl. No. 12/302,738, Final Office Action mailed Oct. 3, 2013", 11 pgs.
"U.S. Appl. No. 12/302,738, Non Final Office Action mailed Jan. 2, 2013", 10 pgs.
"U.S. Appl. No. 12/302,738, Preliminary Amendment filed Nov. 26, 2008", 8 pgs.
"U.S. Appl. No. 12/302,738, Response filed Jun. 26, 2013 to Non Final Office Action mailed Jan. 2, 2013", 10 pgs.
"U.S. Appl. No. 12/302,738, Response filed Nov. 19, 2012 to Restriction Requirement mailed Oct. 19, 2012", pgs.
"U.S. Appl. No. 12/704,343, Advisory Action mailed Apr. 5, 2013", 3 pgs.
"U.S. Appl. No. 12/704,343, Examiner Interview Summary mailed Feb. 7, 2013", 3 pgs.
"U.S. Appl. No. 12/704,343, Examiner Interview Summary mailed Feb. 25, 2013", 3 pgs.
"U.S. Appl. No. 12/704,343, Final Office Action mailed May 10, 2013", 7 pgs.
"U.S. Appl. No. 12/704,343, Final Office Action mailed Dec. 7, 2012", 9 pgs.
"U.S. Appl. No. 12/704,343, Notice of Allowance mailed Aug. 2, 2013", 10 pgs.
"U.S. Appl. No. 12/704,343, Response filed Feb. 27, 2013 to Final Office Action mailed Dec. 7, 2012", 9 pgs.
"U.S. Appl. No. 12/704,343, Response filed Jul. 10, 2013 to Final Office Action mailed May 10, 2013", 8 pgs.
"U.S. Appl. No. 13/736,545, Notice of Allowance mailed Aug. 2, 2013", 9 pgs.
"U.S. Appl. No. 13/736,545, Preliminary Amendment filed Mar. 6, 2013", 3 pgs.
"U.S. Appl. No. 13/791,175, Non Final Office Action mailed Jun. 7, 2013", 10 pgs.
"U.S. Appl. No. 13/791,175, Preliminary Amendment filed Mar. 8, 2013", 4 pgs.
"Aromatic Ions (Chemgapedia)", [online]. [retrieved on Dec. 3, 2012]. Retrieved From Internet: <URL: http://www.chemgapedia.de/vsengine/vlu/vsc/en/ch/12/oc/vlu_organik/aromaten/aromaten/aromaten_gesamt.vlu/Page/vsc/en/ch/12/oc/aromaten/aromaten/ar_ionen/ar_ionen.vscml.html>, (2012), 2 pgs.
"Chinese Application Serial No. 200880011525.8, Response filed Feb. 27, 2013 to Office Action mailed Oct. 16, 2012", (w/ English Translation of Amended Claims), 10 pgs.
"Eurasian Application Serial No. 200901078, Office Action mailed Jan. 29, 2013", (w/ English Translation), 4 pgs.
"Eurasian Application Serial No. 200901078, Response filed Jan. 16, 2013 to Office Action mailed Sep. 18, 2012", (w/ English Translation of Claims), 68 pgs.

(56) References Cited

OTHER PUBLICATIONS

"Eurasian Application Serial No. 200901078, Response filed Jul. 29, 2013 to Office Action mailed Jan. 29, 2013", (w/ English Translation of Claims), 138 pgs.
"European Application Serial No. 06813535.9, Examination Notification Art. 94(3) mailed Sep. 24, 2013", 4 pgs.
"European Application Serial No. 07755916.9, Examination Notification Art. 94(3) mailed Aug. 15, 2013", 4 pgs.
"European Application Serial No. 12004181.9, Communication mailed Oct. 22, 2012", 2 pgs.
"European Application Serial No. 12004181.9, Communication pursuant to Rule 112(1) EPC mailed May 31, 2013", 1 pg.
"European Application Serial No. 12004181.9, Examination Notification Art. 94(3) mailed Sep. 2, 2013", 5 pgs.
"European Application Serial No. 12004181.9, Response filed Jul. 31, 2013 to Communication pursuant to Rule 112(1) EPC mailed May 31, 2013 and Communication mailed Oct. 22, 2012", 9 pgs.
"Indian Application Serial No. 2064/delnp/2008, Examination Report mailed Aug. 21, 2012", 5 pgs.
"Indian Application Serial No. 5675/DELNP/2009, Voluntary Amendment filed Feb. 18, 2011", 7 pgs.
"Israeli Application Serial No. 200240, Examiner Report mailed Aug. 5, 2013", (English Translation), 3 pgs.
"Israeli Application Serial No. 200240, Response filed Dec. 17, 2012 to Examiner Report mailed Aug. 28, 2012", (w/ English Translation of Claims), 4 pgs.
"Japanese Application Serial No. 2008-528017, Response filed Nov. 20, 2012 to Office Action mailed May 22, 2012", (w/ English Translation of Amended Claims), 19 pgs.
"Japanese Application Serial No. 2009-549102, Office Action mailed May 29, 2013", (w/ English Translation), 5 pgs.
"Japanese Application Serial No. 2009-549102, Response filed Mar. 22, 2013 to Office Action mailed Oct. 16, 2012", (w/ English Translation of Amended Claims), 7 pgs.
"Japanese Application Serial No. 2009-549102, Response filed Aug. 20, 2013 to Office Action mailed May 29, 2013", (w/ English Translation of Amended Claims), 5 pgs.
"Japanese Patent Application Serial No. 2008-528017, Office Action mailed May 22, 2012", (English Translation), 4 pgs.
Butler, Roslyn S, et al., "Highly fluorescent donor—acceptor purines", *J. Mater. Chem.*, 17(19), (2007), 1863-1865.
"U.S. Appl. No. 12/302,738, Notice of Allowance mailed Dec. 27, 2013", 9 pgs.
"U.S. Appl. No. 12/302,738, Response filed Dec. 3, 2013 to Final Office Action mailed Oct. 3, 2013", 8 pgs.
"U.S. Appl. No. 12/704,343, Notice of Allowance mailed Jan. 3, 2014", 11 pgs.
"U.S. Appl. No. 13/791,175, Final Office Action mailed Dec. 26, 2013", 12 pgs.
"U.S. Appl. No. 13/791,175, Response filed Nov. 1, 2013 to Non Final Office Action mailed Jun. 7, 2013", 8 pgs.
"International Application Serial No. PCT/US06/32371, International Preliminary Report on Patentability mailed Mar. 6, 2008", 6 pgs.
"Israeli Application Serial No. 200240, Response filed Nov. 25, 2013 to Examiner Report mailed Aug. 5, 2013", 8 pgs.
Anders, H.-J., et al., "Molecular mechanisms of autoimmunity triggered by microbial infection", *Arthritis Research & Therapy*, 7(5), (2005), 215-224.
Staros, E. B., et al., "New Approaches to Understanding Its Clinical Significance", *Am. J. Clin. Pathol.*, 123(2) (2005), 305-312.
Takeda, K., et al., "Toll-like receptors in innate immunity", *International Immunology*, 17(1), (2005), 1-14.

U.S. Appl. No. 12/302,738, Notice of Allowance mailed Apr. 22, 2014, 7 pgs.
U.S. Appl. No. 12/367,172, Final Office Action mailed Apr. 21, 2015, 19 pgs.
U.S. Appl. No. 12/367,172, Non Final Office Action mailed Jul. 1, 2014, 20 pgs.
U.S. Appl. No. 12/367,172, Response filed Dec. 29, 2014 to Non Final Office Action mailed Jul. 1, 2014, 7 pgs.
U.S. Appl. No. 13/736,545, Notice of Allowance mailed Mar. 18, 2014, 6 pgs.
U.S. Appl. No. 13/791,175, Final Office Action mailed Nov. 20, 2014, 12 pgs.
U.S. Appl. No. 13/791,175, Non Final Office Action mailed Jul. 21, 2014, 11 pgs.
U.S. Appl. No. 13/791,175, Response filed Jun. 26, 2014 to Final Office Action mailed Dec. 26, 2013, 9 pgs.
U.S. Appl. No. 13/791,175, Response filed Oct. 21, 2014 to Non Final Office Action mailed Jul. 21, 2014, 7 pgs.
U.S. Appl. No. 14/309,245, Notice of Allowance mailed Jan. 20, 2015, 12 pgs.
Australian Application Serial No. 2008227128, Secondary Amendment filed Jan. 9, 2012, 16 pgs.
Canadian Application Serial No. 2,677,733 Response filed Feb. 16, 2015 to Office Action mailed Aug. 25, 2014, 6 pgs.
Canadian Application Serial No. 2,677,733, Office Action mailed Aug. 25, 2014, 2 pgs.
"Definition: Micelle", Merriam-Webster, [Online]. Retrieved from the Internet: <URL:http://www.merriam-webster.com/dictionary/micelle>, (Accessed on Jun. 25, 2014), 1 pg.
European Application Serial No. 06813535.9, Response filed Apr. 4, 2014 to Examination Notification Art. 94(3) mailed Sep. 24, 2013, 70 pgs.
European Application Serial No. 07755916.9, Office Action mailed Mar. 25, 2014, 1 pg.
European Application Serial No. 07755916.9, Response filed May 23, 2014 to Examination Notification Art. 94(3) mailed Aug. 15, 2013, 13 pgs.
European Application Serial No. 12004181.9 Response Filed Dec. 15, 2014 to Non-Final Office Action Mailed Jul. 18, 2014, 138 pgs.
European Application Serial No. 12004181.9, Examination Notification Art. 94(3) mailed Jul. 18, 2014, 4 pgs.
European Application Serial No. 12004181.9, Response filed Mar. 7, 2014 to Examination Notification Art. 94(3) mailed Sep. 2, 2013, 10 pgs.
European Application Serial No. 13001957.3, Extended European Search Report mailed Jan. 28, 2014, 17 pgs.
European Application Serial No. 13001957.3, Office Action mailed Mar. 3, 2014, 2 pgs.
European Application Serial No. 13001957.3, Response filed Aug. 20, 2014 Extended European Search Report mailed Jan. 28, 2014, Includes Response Office Action mailed Mar. 3, 2014, 7 pgs.
Indian Application Serial No. 5675/DELNP/2009, First Examiner Report mailed Sep. 11, 2014, 2 pgs.
Japanese Application Serial No. 2013-59721, Office Action mailed May 30, 2014, w/English translation, 10 pgs.
Korean Application Serial No. 10-2009-7018499, Office Action mailed Sep. 17, 2014, 8 pgs.
Jacobson, Kenneth A, et al., "Adenosine analogs with covalently attached lipids have enhanced potency at Al-adenosine receptors", FEBS Letters, 225(1-2), (1987), 97-102.
Kurimoto, A., et al., "Synthesis and evaluation of 2-substituted 8-hydroxyadenines as potent interferon inducers with improved oral bioavailabilities", Bioorg Med Chem., 12(5), (Mar. 1, 2004), 1091-9.
Takeda, K., et al., "Toll-like receptors", Annu Rev Immunol., 21, (2003), 335-76.

\* cited by examiner

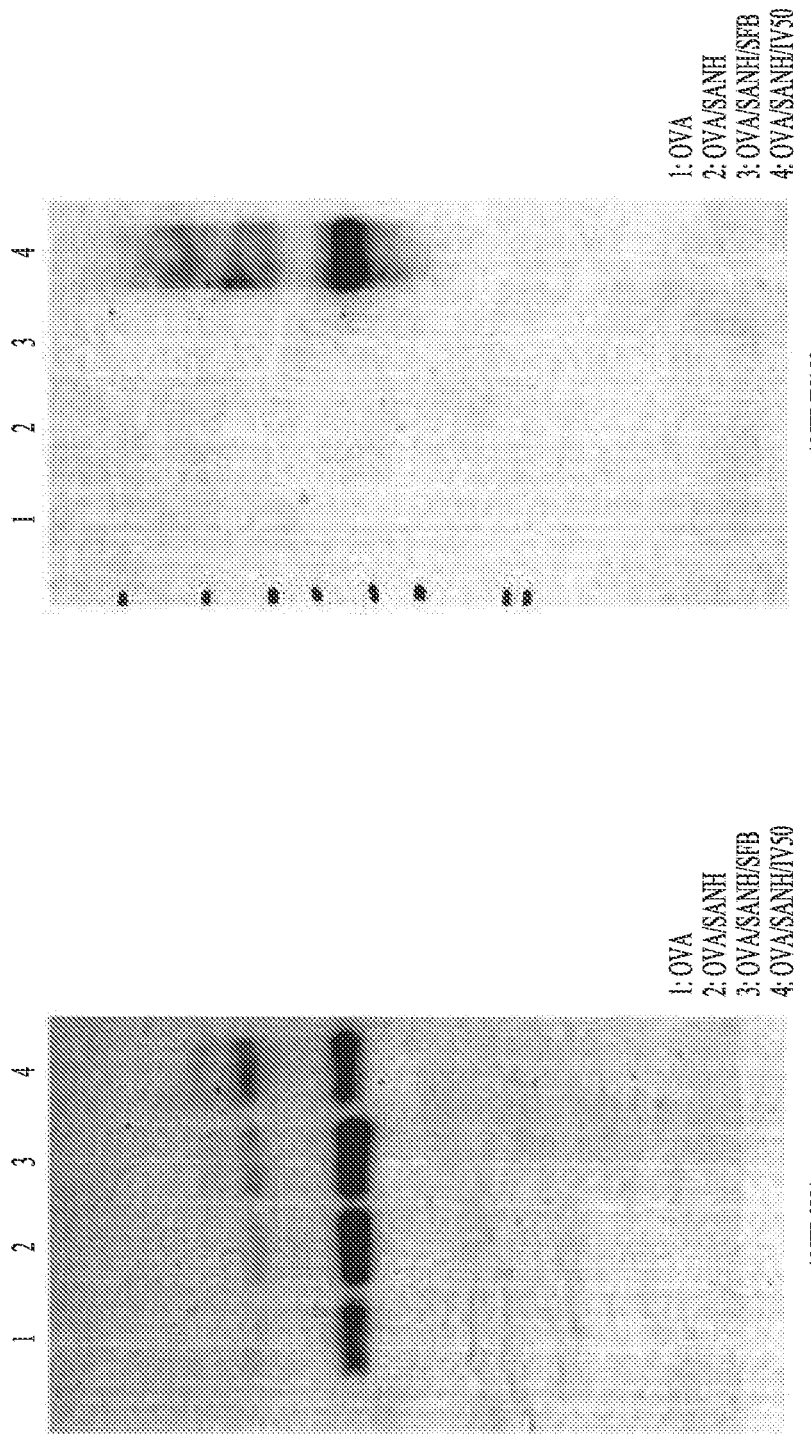

TLR AGONISTS

RELATED APPLICATION

This application is a continuation of U.S. patent application Ser. No. 12/064,529, filed Feb. 5, 2009, which is a U.S. National Stage Filing under 35 U.S.C. 371 from International Application Number PCT/US2006/032371, filed Aug. 21, 2006 and published in English as WO 2007/024707 on Mar. 1, 2007, which claims the benefit of priority from U.S. Provisional Application Ser. No. 60/710,337 filed Aug. 22, 2005, under 35 U.S.C. 119(e), which applications and publication are herein incorporated by reference in their entirety.

GOVERNMENT FUNDING

The invention was made with government support under Grant Number AI57436 awarded by the National Institutes of Health. The government has certain rights in the invention.

BACKGROUND OF THE INVENTION

A great deal has been learned about the molecular basis of innate recognition of microbial pathogens in the last decade. It is generally accepted that many somatic cells express a range of pattern recognition receptors that detect potential pathogens independently of the adaptive immune system. (See Janeway et al., Annu Rev Immunol, 20:197-216 (2002).) These receptors are believed to interact with microbial components termed pathogen associated molecular patterns (PAMPs). Examples of PAMPs include peptidoglycans, lipotechoic acids from gram-positive cell walls, the sugar mannose (which is common in microbial carbohydrates but rare in humans), bacterial DNA, double-stranded RNA from viruses, and glucans from fungal cell walls. PAMPs generally meet certain criteria that include, (a) their expression by microbes but not their mammalian hosts, (b) conservation of structure across the wide range of pathogens, and (c) the capacity to stimulate innate immunity. Toll-like Receptors (TLRs) have been found to play a central role in the detection of PAMPs and in the early response to microbial infections. (See Underhill et al., Curr Opin Immunol, 14:103-110 (2002).) Ten mammalian TLRs and a number of their agonists have been identified. For example, TLR7 and TLR9 recognize and respond to imiquimod and immunostimulatory CpG oligonucleotides (ISS-ODN), respectively. The synthetic immunomodulator R-848 (resiquimod) activates both TLR7 and TLR8. While TLR stimulation initiates a common signaling cascade (involving the adaptor protein MyD88, the transcription factor NF-kB, and pro-inflammatory and effector cytokines), certain cell types tend to produce certain TLRs. For example, TLR7 and TLR9 are found predominantly on the internal faces of endosomes in dendritic cells (DCs) and B lymphocytes (in humans; mouse macrophages express TLR7 and TLR9). TLR8, on the other hand, is found in human blood monocytes. (See Hornung et al., J Immunol, 168:4531-4537 (2002)).

Interferons (INFs) are also involved in the efficient induction of an immune response, especially after viral infection (Brassard et al., J. Leukoc Biol, 71:568-581 (2002).) However, many viruses produce a variety of proteins that block interferon production or action at various levels. Antagonism of interferon is believed to be part of a general strategy to evade innate, as well as adaptive immunity. (See Levy et al., Cytokine Growth Factor Rev, 12:143-156 (2001).) While TLR agonists (TLR-L) may be sufficiently active for some methods of treatment, in some instances the microbial interferon antagonists could mitigate the adjuvant effects of synthetic TLR-L.

Accordingly, there exists a need for compounds that augment TLR-induced signal transduction, i.e., compounds that hinder viral or bacterial obstruction of interferon production or have the ability to modulate the innate immune system using the TLR agonists.

SUMMARY OF THE INVENTION

The present invention provides for TLR agonist conjugates (compounds) and compositions, as well as methods of using them. The compounds of the invention are broad-spectrum, long-lasting, and non-toxic combination of synthetic immunostimulatory agents, which are useful for activating the immune system of a mammal, preferably a human and can help direct the pharmacophore to the receptor within the endosomes of target cells and enhance the signal transduction induced by the pharmacophore. The compounds of the invention include a pharmacophore covalently bound to an auxiliary group. Accordingly there is provided a compound of the invention which is a compound of formula (I):

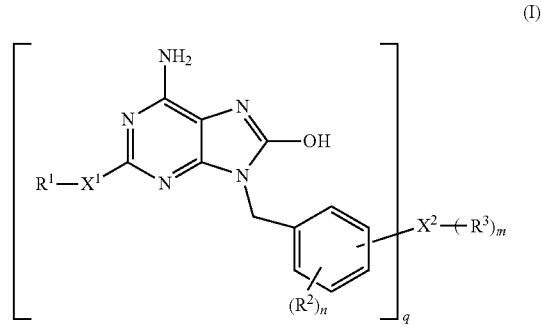

wherein $X^1$ is —O—, —S—, or —NR$^c$—;

wherein R$^c$ hydrogen, $C_{1-10}$alkyl, or $C_{1-10}$alkyl substituted by $C_{3-6}$-cycloalkyl, or R$^c$ and R$^1$ taken together with the nitrogen atom can form a heterocyclic ring or a substituted heterocyclic ring, wherein the substituents are hydroxy, $C_{1-6}$alkyl, hydroxy$C_{1-6}$alkylene, $C_{1-6}$alkoxy, $C_{1-6}$alkoxy$C_{1-6}$alkylene, or cyano;

$R^1$ is $(C_1-C_{10})$alkyl, substituted $(C_1-C_{10})$alkyl, $C_{6-10}$aryl, or substituted $C_{6-10}$aryl, $C_{5-9}$heterocyclic, substituted $C_{5-9}$heterocyclic;

each $R^2$ is independently hydrogen, —OH, $(C_1-C_6)$alkyl, substituted $(C_1-C_6)$alkyl, $(C_1-C_6)$alkoxy, substituted $(C_1-C_6)$alkoxy, —C(O)—$(C_1-C_6)$alkyl (alkanoyl), substituted —C(O)—$(C_1-C_6)$alkyl, —C(O)—$(C_6-C_{10})$aryl (aroyl), substituted —C(O)—$(C_6-C_{10})$aryl, —C(O)OH (carboxyl), —C(O)O$(C_1-C_6)$alkyl (alkoxycarbonyl), substituted —C(O)O$(C_1-C_6)$alkyl, —NR$^a$R$^b$, —C(O)NR$^a$R$^b$ (carbamoyl), substituted —C(O)NR$^a$R$^b$, halo, nitro, or cyano;

each R$^a$ and R$^b$ is independently hydrogen, $(C_1-C_6)$alkyl, $(C_3-C_8)$cycloalkyl, $(C_1-C_6)$alkoxy, halo$(C_1-C_6)$alkyl, $(C_3-C_8)$cycloalkyl$(C_1-C_6)$alkyl, $(C_1-C_6)$alkanoyl, hydroxy$(C_1-C_6)$alkyl, aryl, aryl$(C_1-C_6)$alkyl, Het, Het $(C_1-C_6)$alkyl, or $(C_1-C_6)$alkoxycarbonyl;

$X^2$ is a bond or a linking group; and $R^3$ is an auxiliary group;

n is 1, 2, 3, or 4; m is 1 or 2; q is 1 or 2; or a pharmaceutically acceptable salt thereof.

The auxiliary groups can include organic molecules, composed of carbon, oxygen, hydrogen, nitrogen, sulfur, phosphorus atoms. These groups are not harmful to body tissues (e.g., they are non-toxic, and/or do not cause inflammation).

In addition, the invention also provides a pharmaceutical composition comprising at least one compound of formula (I), or a pharmaceutically acceptable salt thereof, in combination with a pharmaceutically acceptable diluent or carrier.

In one embodiment, the invention provides a therapeutic method for preventing or treating a pathological condition or symptom in a mammal, such as a human, wherein the activity of TLR agonists is implicated and its action is desired, comprising administering to a mammal in need of such therapy, an effective amount of a compound of formula (I), or a pharmaceutically acceptable salt thereof. Non-limiting examples of pathological conditions or symptoms that are suitable for treatment include cancers, treatment for bacterial or viral diseases, treating autoimmune diseases, and treating Crohn's Disease.

The compounds of the invention can also be used as or to prepare vaccines against bacteria, viruses, cancer cells, cancer specific peptides, enhancers of monoclonal antibodies against cancer, a CNS stimulant, or for biodefense.

The invention provides a compound of formula (I) for use in medical therapy (e.g., for use as an anti-cancer agent, treatment for bacterial diseases, treatment for viral diseases, such as hepatitis C and hepatitis B, Crohn's Disease, and as therapeutic agents for treating immunologic disease). Furthermore, it is suggested that compounds of formula (I) will prevent carcinogenesis by hepatitis C and hepatitis B, as well as the use of a compound of formula (I) for the manufacture of a medicament useful for the treatment of cancer, viral diseases, Crohn's Disease, and immunologic disorders in a mammal, such as a human.

In a specific embodiment, the present invention provides a method for treating a viral infection in a mammal by administering a TLR agonist compound of formula (I). The viral infection can be caused by an RNA virus, a product of the RNA virus that acts as a TLR agonist and/or a DNA virus. A specific DNA virus for treatment is the Hepatitis B virus.

In another specific embodiment, the present invention provides a method for treating cancer by administering an effective amount of a TLR agonist compound of formula (I). The cancer can be an interferon sensitive cancer, such as, for example, a leukemia, a lymphoma, a myeloma, a melanoma, or a renal cancer.

In another specific embodiment, the present invention provides a method of treating an autoimmune disease by administering a therapeutically effective amount of a TLR agonist compound of formula (I) or a pharmaceutically acceptable salt of such a compound. A specific autoimmune disease is Multiple Sclerosis, lupus, rheumatoid arthritis and the like.

In another specific embodiment, the present invention provides a method of treating Crohn's Disease by administering a TLR agonist compound of formula (I).

The TLR agonists can be a homofunctional TLR agonist polymer and can consist of a TLR-7 agonist or a TLR-8 agonist. The TLR7 agonist can be a 7-thia-8-oxoguanosinyl (TOG) moiety, a 7-deazaguanosinyl (7DG) moiety, a resiquimod moiety, or an imiquimod moiety. The TLR8 agonist can be a resiquimod moiety. In another aspect, the TLR agonist is a heterofunctional TLR agonist polymer. The heterofunctional TLR agonist polymer can include a TLR-7 agonist and a TLR-8 agonist or a TLR-9 agonist or all three agonists. The heterofunctional TLR agonist polymer can include a TLR-8 agonist and a TLR-9 agonist.

The invention also provides processes and intermediates disclosed herein that are useful for preparing compounds of formula (I) or salts thereof.

BRIEF DESCRIPTION OF THE FIGURES

FIGS. 13A and 13B illustrate the distinction between the four substances applied to the respective lanes on a gel in a Western plot analysis. In FIG. 13A, the gel membrane was probed with anti-ovalbumin (anti-OVA) antibody and all lanes gave a positive band, indicating that OVA was detected in all lanes, as expected. In FIG. 13B, the gel membrane was probed with the selective antibody raised to the TLR ligand portion of the conjugate, and therefore only lane 4 was positive, confirming the specificity of the antibody for the TLR ligand.

DETAILED DESCRIPTION

Figure 1:
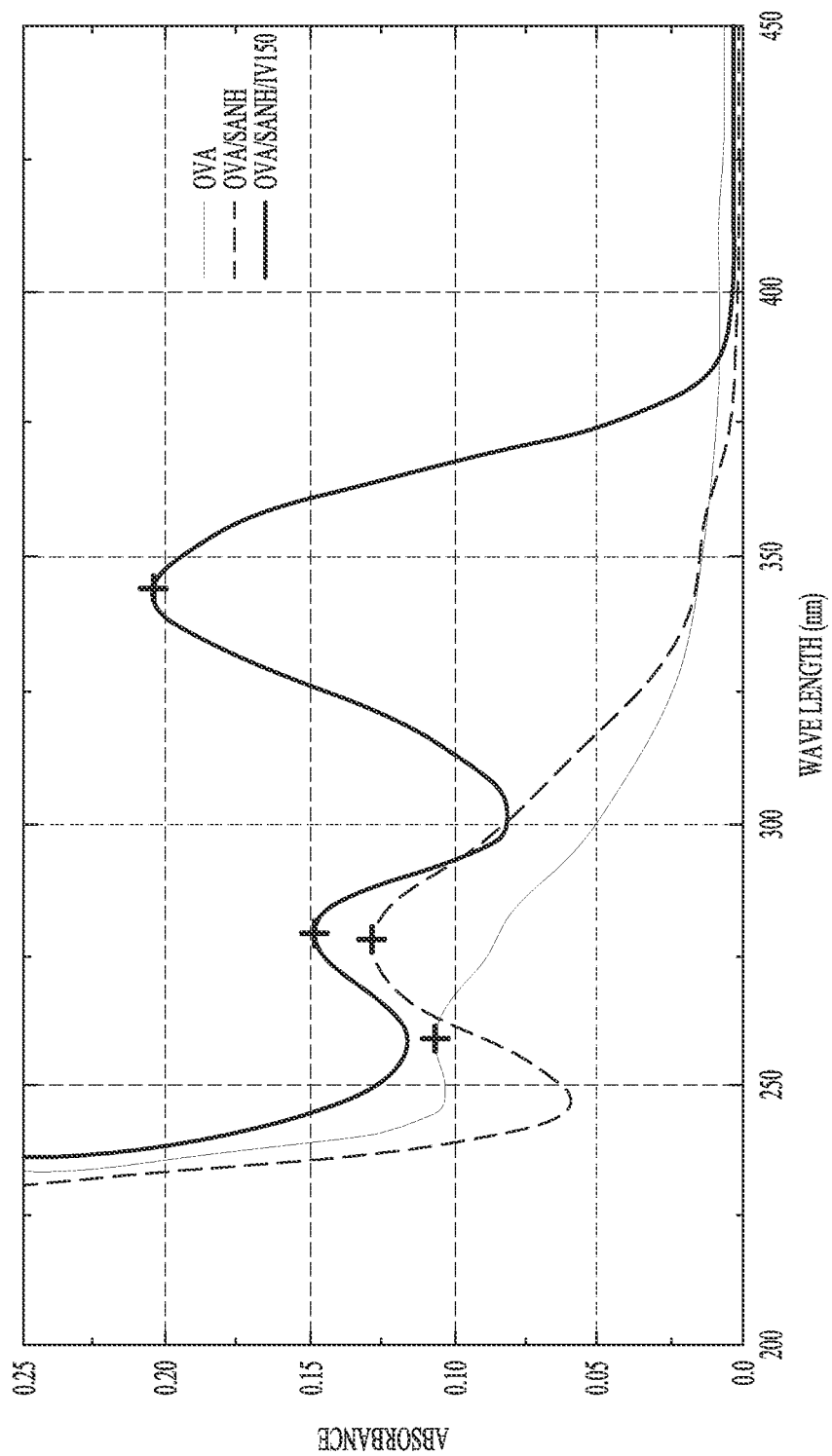
FIG. 1 is a graphic illustration of the absorption chromophore (at ~350 nm) of a compound of formula I (OVA/IV150 Conjugate).
Figure 2:
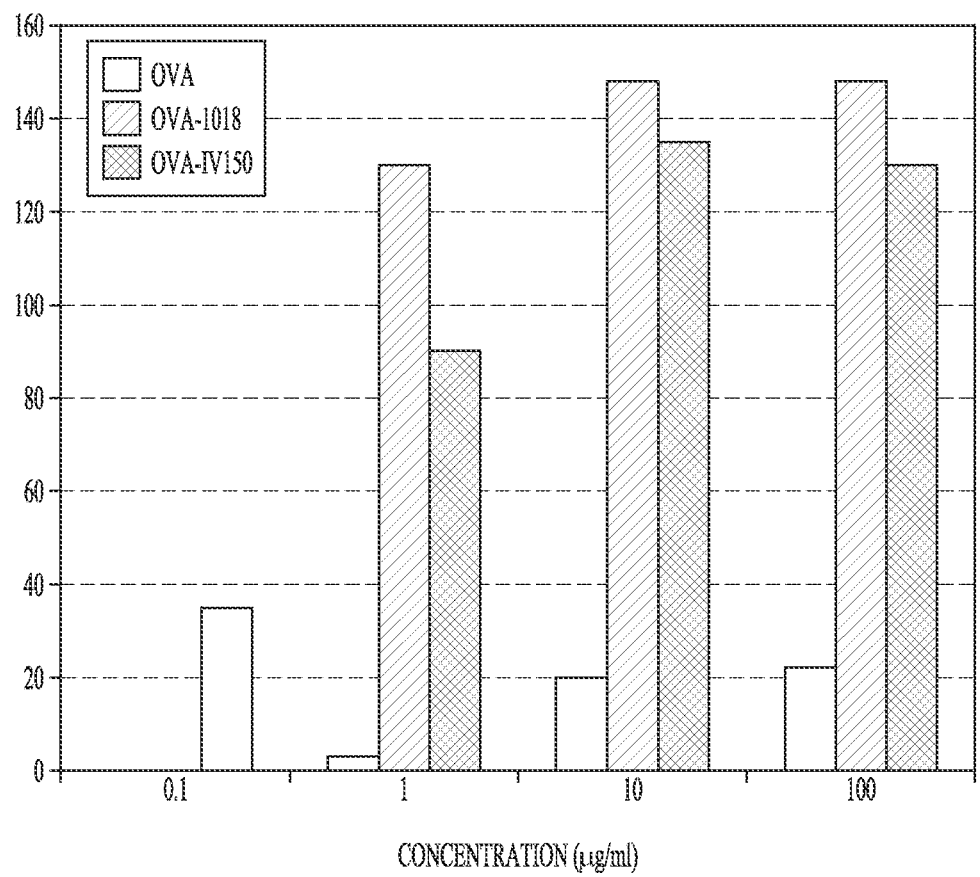
FIG. 2 is a graphic illustration of the stimulation of bone marrow derived dendritic cells (BMDC).
Figure 3:
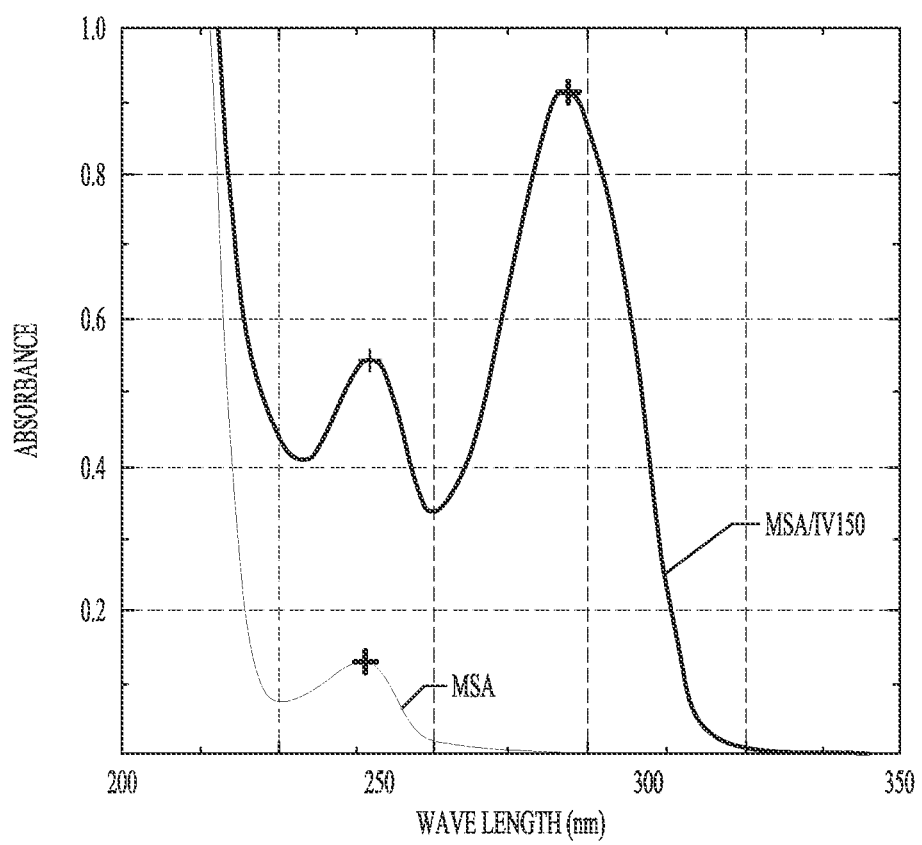
FIG. 3 illustrates the conjugation of a TLR7 agonist, UC-1V150, to mouse serum albumin (MSA). The success of conjugation is indicated by UV spectroscopy. The UC-1V150 to MSA ratio is approximately 5:1
Figure 4A:
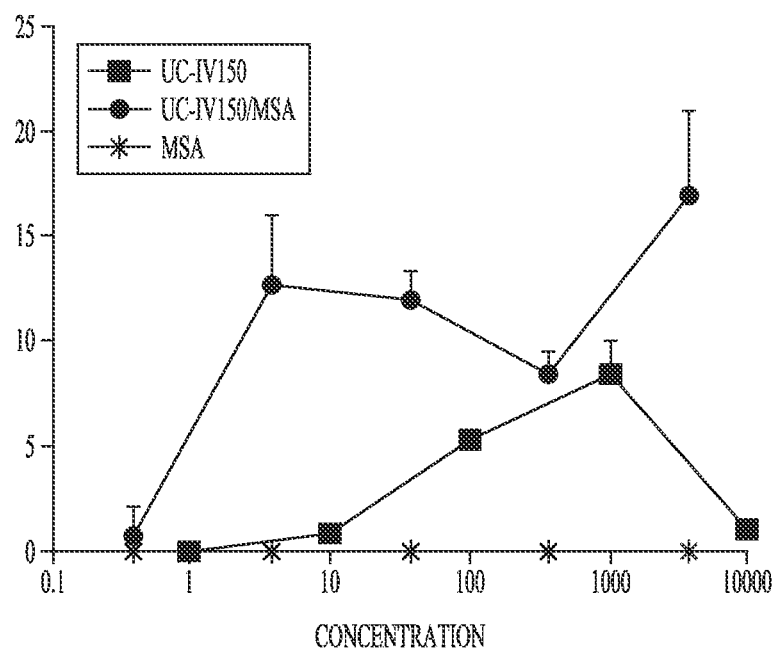
FIGS. 4A and B illustrate that the UC-1V150 and MSA conjugates activate both murine bone marrow-derived macrophages (4A) and human peripheral blood mononuclear cells (4B). Cells were incubated with various concentrations of the compound from 0.5 nM to 10 µM in BMDM or from 0.1 to 10 µM in PBMC. Culture supernatants were harvested after 24 h and cytokine levels were analyzed by Luminex.
Figure 4B:
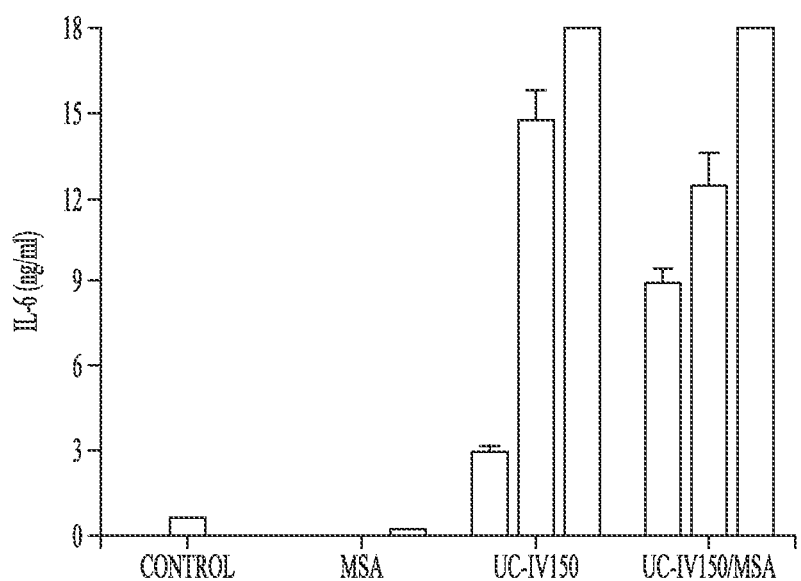
Figure 5A:
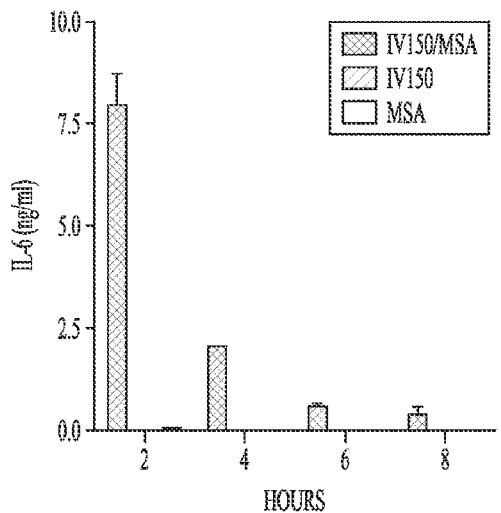
FIGS. 5A, 5B, 5C, and 5D illustrate the increased potency and duration of effect of UC-1V150/MSA. C57BL/6 mice were injected (i.v.) with (A) 0.1 micromole of SM-360320, a TLR7 ligand, or (B) equivalent amount of a TLR7 agonist UC-1V150 (aldehyde-modified SM-360320) or UC-1V150/MSA to 500 µg MSA per mouse. Serum samples were collected at the indicated time points and cytokine levels were analyzed by Luminex. MSA=mouse serum albumin. The effect from the original TLR7 ligand, SM-360320, lasted for only 2 hours whereas UC-1V150/MSA has extended the effect to at least 6 hours.
Figure 5B:
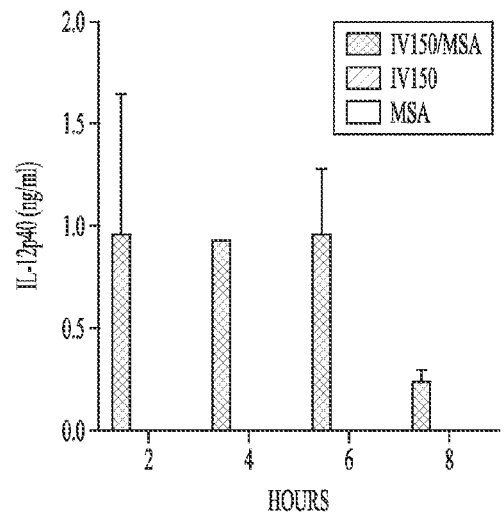
Figure 5C:
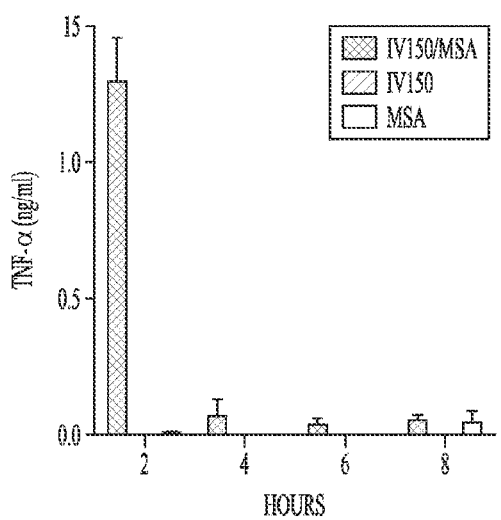
Figure 5D:
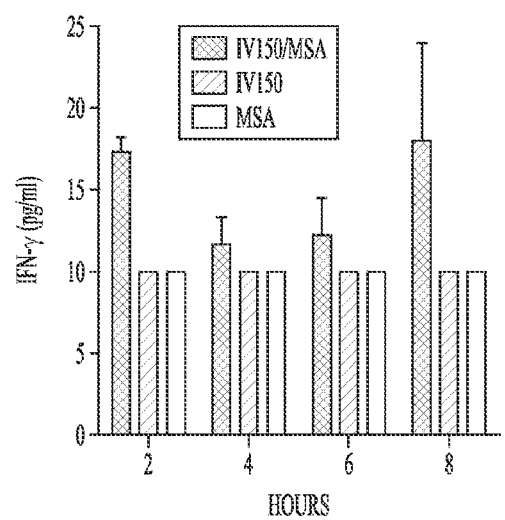
Figure 6A:
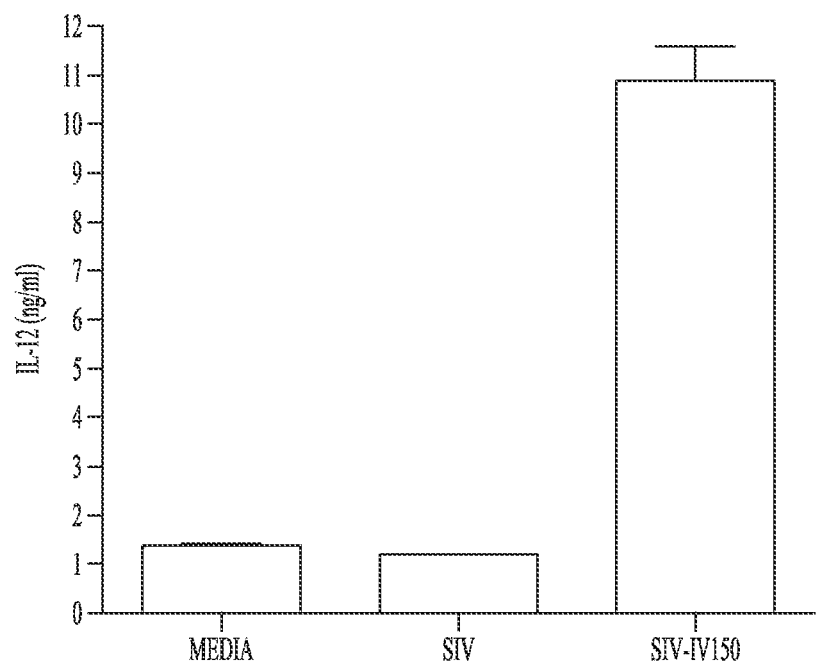
FIG. 6 illustrates the effects of UC-1V150 conjugated with inactivated SIV (6A) or with OVA in combination with ODN (6B). Myeloid BMDC were incubated for 24 hr with various conditions at 0.1 µg/ml as indicated. IL-12 levels in the cell supernatant were measured by ELISA.
Figure 6B:
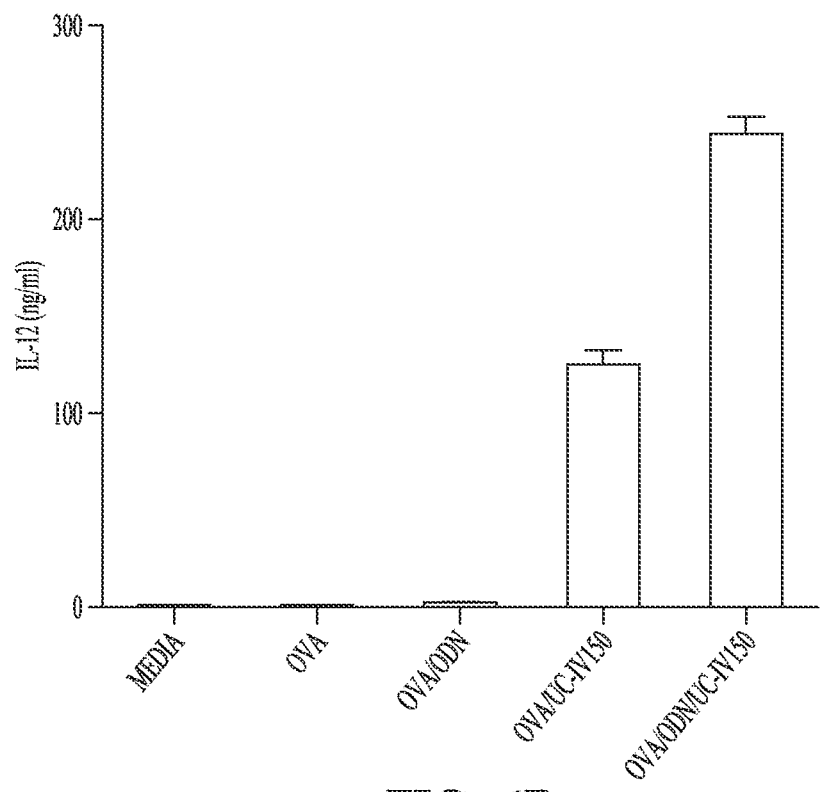
Figure 7A:
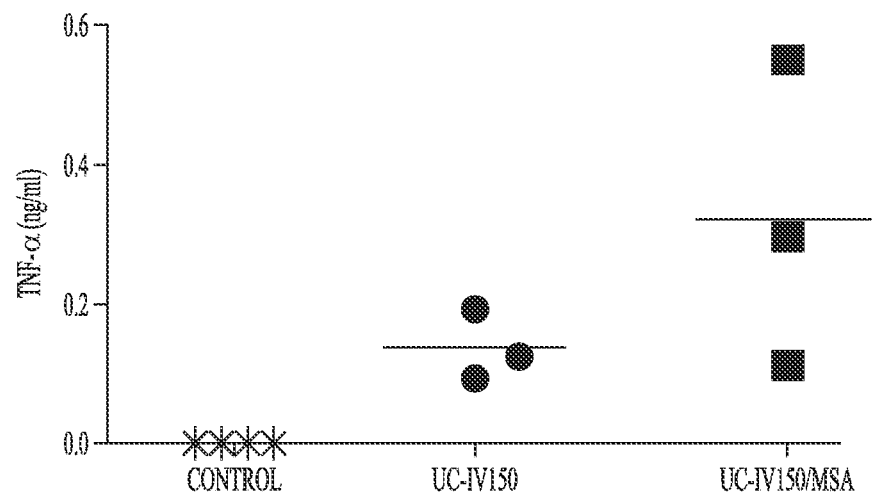
FIGS. 7A and 7B illustrates an increased potency of UC-1V150/MSA. C57BL/6 mice were i.v. injected with 380 nmole of SM-360320 or UC-1V150, or 500 µg of UC-1V150/MSA (equivalent to 3.8 nmole UC-1V150) per mouse. Serum samples were collected after 2 h and cytokine levels were analyzed by Luminex. To achieve the similar effect, at least 100-fold higher concentration of either UC-1V150 or SM-360320 was required as compared to that of UC-1V150/MSA.
Figure 7B:
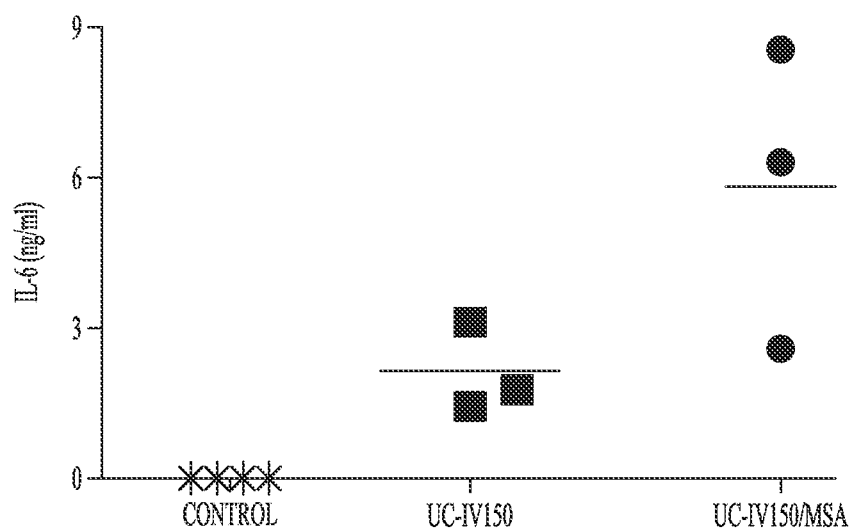
Figure 8:
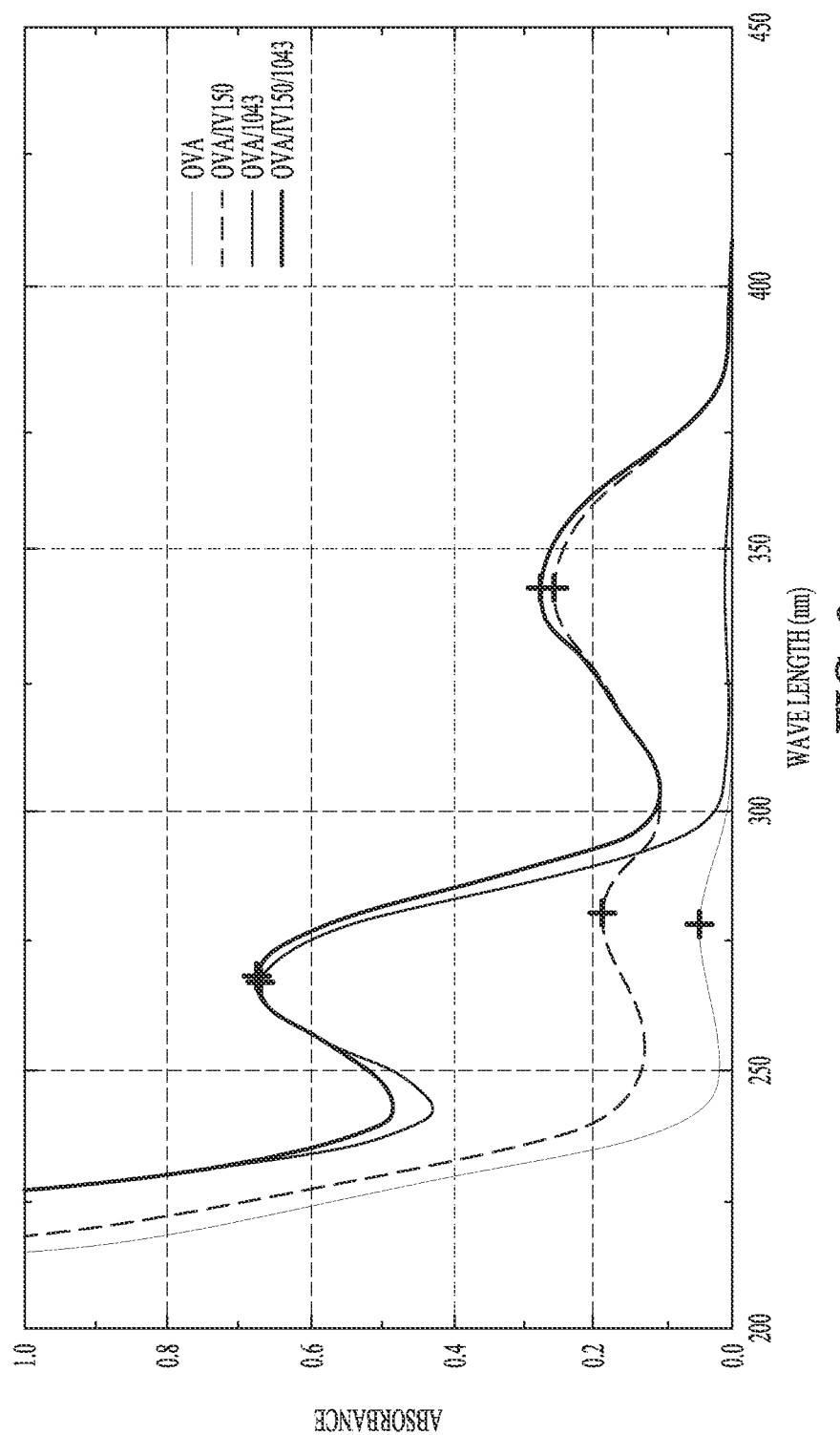
FIG. 8 is an illustration of the uv spectrum of a double-conjugate, (OVA/IV150/1043).
Figure 9:
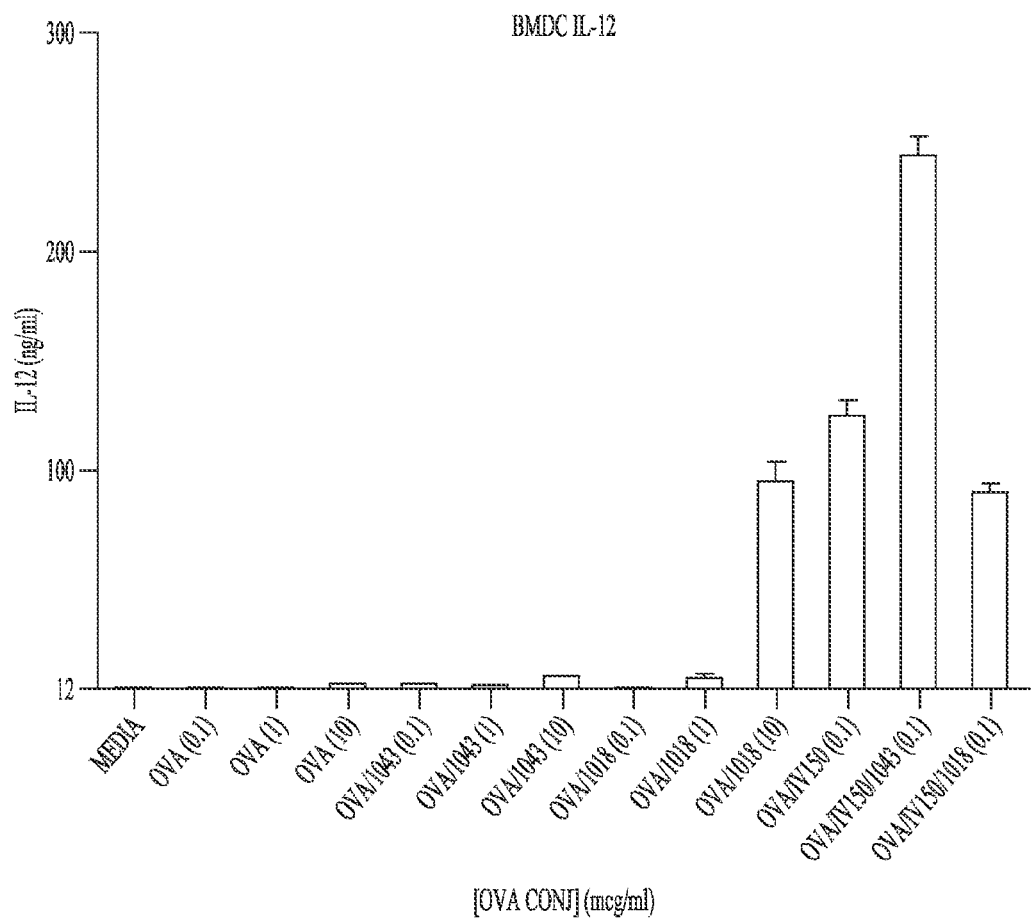
FIG. 9 is an illustration of the induction of IL-12 in BMDC using OVA/ODN/IV150 conjugates.
Figure 10:
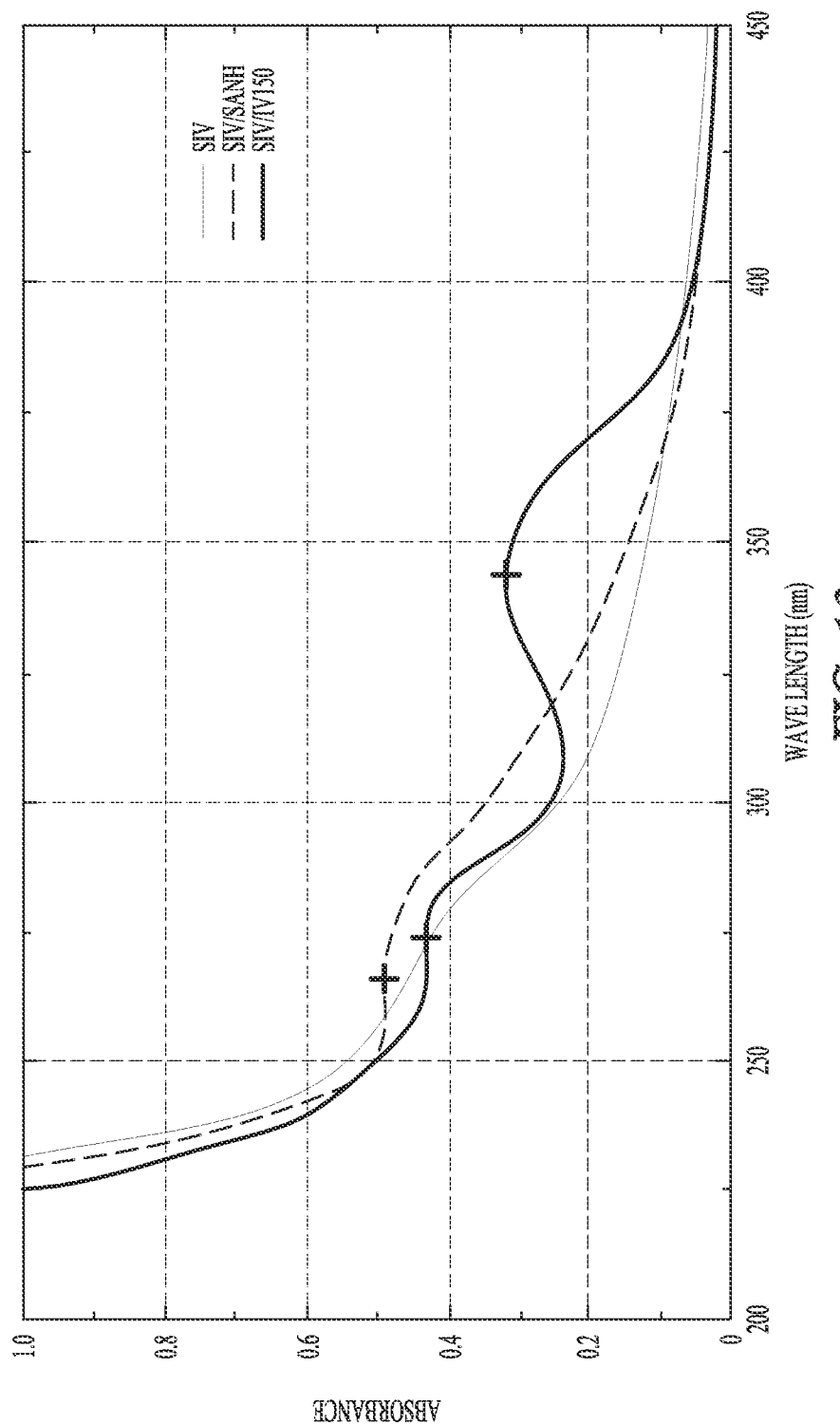
FIG. 10 illustrates direct conjugation of SIV Particles to the IA compound IV150.
Figure 11:
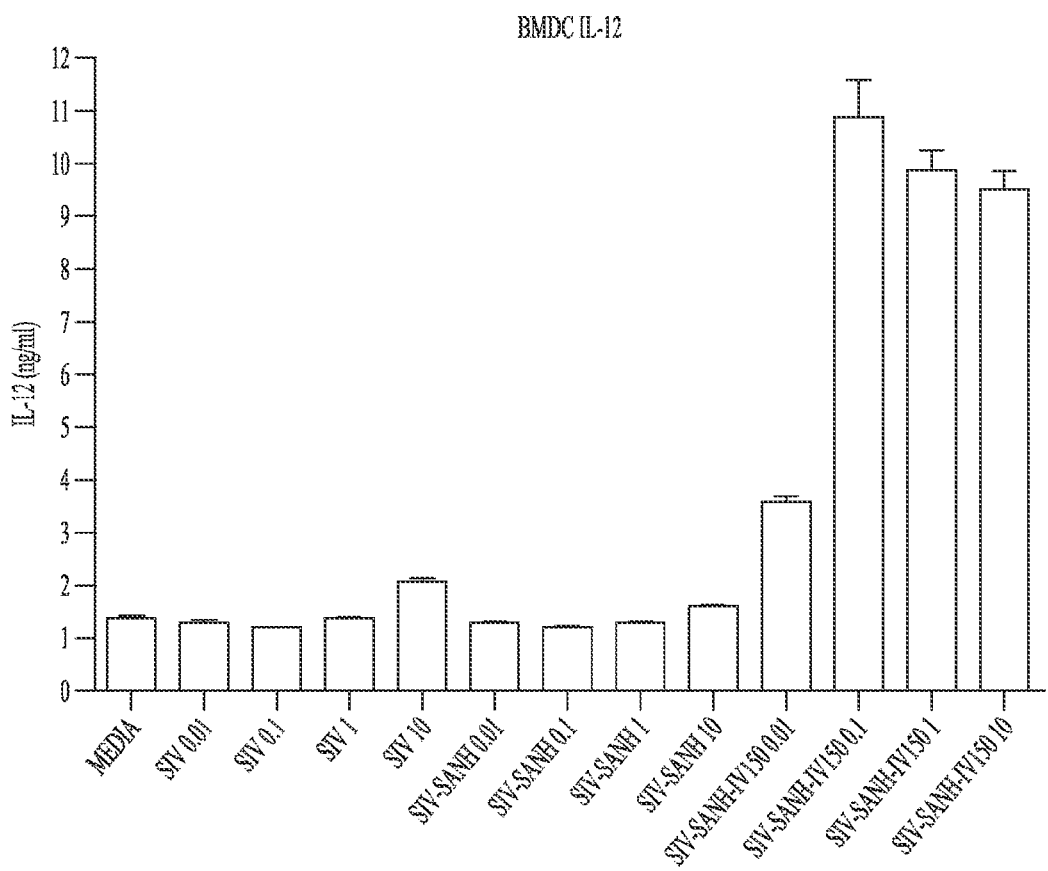
FIG. 11 illustrates the ability to prepare compounds of the invention with virus particles attached to a compound having formula IA and the TLR agonist activity of the compounds.
Figure 12:
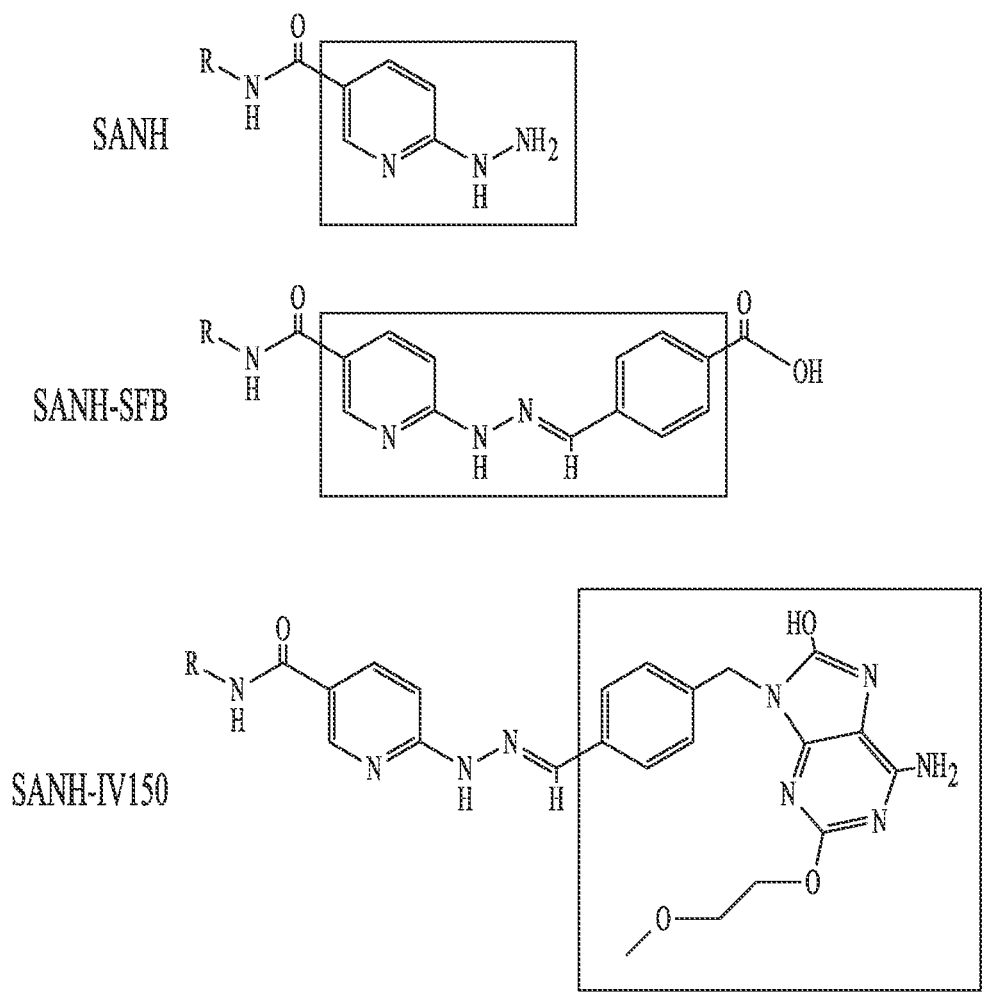
FIG. 12 illustrates the molecular areas of specificity for antibodies raised against the conjugates containing a linker and a TLR ligand.

Non-limiting examples of auxiliary groups include side chains that increase solubility, such as, for example, groups containing morpholino, piperidino, pyrrolidino, or piperazino rings and the like; amino acids, polymers of amino acids (proteins or peptides), e.g., dipeptides or tripeptides, and the like; carbohydrates (polysaccharides), nucleotides such as, for example, PNA, RNA and DNA, and the like; polymers of organic materials, such as, for example, polyethylene glycol, poly-lactide and the like; monomeric and polymeric lipids; insoluble organic nanoparticles; non-toxic body substances such as, for example, cells, lipids, vitamins, co-factors, antigens such as, for example microbes, such as, for example, viruses, bacteria, fungi, and the like. The antigens can include inactivated whole organisms, or sub-components thereof and the like.

The compounds of the invention can be prepared using compounds having formula (IA):

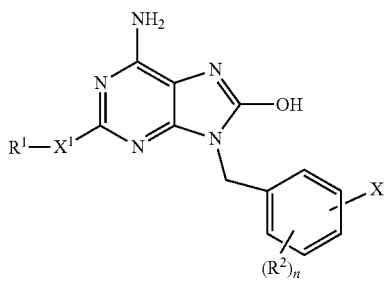

IA where X is a group that can react to form a bond to the linking group or can react to form a bond to the auxiliary group. A specific group of compounds having formula (IA) are disclosed in U.S. Pat. No. 6,329,381.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine nicotine agonist activity using the standard tests described herein, or using other similar tests which are well known in the art.

Processes for preparing compounds of formula I or for preparing intermediates useful for preparing compounds of formula I are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Alkyl includes straight or branched $C_{1-10}$ alkyl groups, e.g., methyl, ethyl, propyl, butyl, pentyl, isopropyl, isobutyl, 1-methylpropyl, 3-methylbutyl, hexyl, and the like.

Lower alkyl includes straight or branched $C_{1-6}$ alkyl groups, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, and the like.

The term "alkylene" refers to a divalent straight or branched hydrocarbon chain (e.g. ethylene —$CH_2$—$CH_2$—).

$C_{3-7}$ Cycloalkyl includes groups such as, cyclopropyl, cyclopentyl, cyclohexyl, cycloheptyl, and the like, and alkyl-substituted $C_{3-7}$ cycloalkyl group, preferably straight or branched $C_{1-6}$ alkyl group such as methyl, ethyl, propyl, butyl or pentyl, and $C_{5-7}$ cycloalkyl group such as, cyclopentyl or cyclohexyl, and the like.

Lower alkoxy includes $C_{1-6}$ alkoxy groups, such as methoxy, ethoxy or propoxy, and the like.

Lower alkanoyl includes $C_{1-6}$ alkanoyl groups, such as formyl, acetyl, propanoyl, butanoyl, pentanoyl or hexanoyl, and the like.

$C_{7-11}$ aroyl, includes groups such as benzoyl or naphthoyl;

Lower alkoxycarbonyl includes $C_{2-7}$ alkoxycarbonyl groups, such as methoxycarbonyl, ethoxycarbonyl or propoxycarbonyl, and the like.

Lower alkylamino group means amino group substituted by $C_{1-6}$ alkyl group, such as, methylamino, ethylamino, propylamino, butylamino, and the like.

Di(lower alkyl)amino group means amino group substituted by the same or different and $C_{1-6}$ alkyl group (e.g. dimethylamino, diethylamino, ethylmethylamino).

Lower alkylcarbamoyl group means carbamoyl group substituted by $C_{1-6}$ alkyl group (e.g. methylcarbamoyl, ethylcarbamoyl, propylcarbamoyl, butylcarbamoyl).

Di(lower alkyl)carbamoyl group means carbamoyl group substituted by the same or different and $C_{1-6}$ alkyl group (e.g. dimethylcarbamoyl, diethylcarbamoyl, ethylmethylcarbamoyl).

Halogen atom means halogen atom such as fluorine atom, chlorine atom, bromine atom or iodine atom.

Aryl refers to a $C_{6-10}$ monocyclic or fused cyclic aryl group, such as phenyl, indenyl, or naphthyl, and the like.

Heterocyclic refers to monocyclic saturated heterocyclic groups, or unsaturated monocyclic or fused heterocyclic group containing at least one heteroatom, e.g., 0-3 nitrogen atoms (—$NR^d$—), 0-1 oxygen atom (—O—), and 0-1 sulfur atom (—S—). Non-limiting examples of saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Non-limiting examples of unsaturated monocyclic heterocyclic group includes 5 or 6 membered unsaturated heterocyclic group, such as furyl, pyrrolyl, pyrazolyl, imidazolyl, thiazolyl, thienyl, pyridyl or pyrimidinyl. Non-limiting examples of unsaturated fused heterocyclic groups includes unsaturated bicyclic heterocyclic group, such as indolyl, isoindolyl, quinolyl, benzothizolyl, chromanyl, benzofuranyl, and the like.

$R^c$ and $R^1$ taken together with the nitrogen atom to which they are attached can form a heterocyclic ring. Non-limiting examples of heterocyclic rings include 5 or 6 membered saturated heterocyclic rings, such as 1-pyrrolidinyl, 4-morpholinyl, 1-piperidyl, 1-piperazinyl or 1-pyrazolidinyl, 5 or 6 membered unsaturated heterocyclic rings such as 1-imidazolyl, and the like.

The alkyl, aryl, heterocyclic groups of $R^1$ can be optionally substituted with one or more substituents, wherein the substituents are the same or different, and include lower alkyl; cycloalkyl, hydroxyl; hydroxy $C_{1-6}$ alkylene, such as hydroxymethyl, 2-hydroxyethyl or 3-hydroxypropyl; lower alkoxy; $C_{1-6}$ alkoxy $C_{1-6}$ alkyl, such as 2-methoxyethyl, 2-ethoxyethyl or 3-methoxypropyl; amino; alkylamino; dialkyl amino; cyano; nitro; acyl; carboxyl; lower alkoxycarbonyl; halogen; mercapto; $C_{1-6}$ alkylthio, such as, methylthio, ethylthio, propylthio or butylthio; substituted $C_{1-6}$ alkylthio, such as methoxyethylthio, methylthioethylthio, hydroxyethylthio or chloroethylthio; aryl; substituted $C_{6-10}$ monocyclic or fused-cyclic aryl, such as 4-hydroxyphenyl, 4-methoxyphenyl, 4-fluorophenyl, 4-chlorophenyl or 3,4-dichlorophenyl; 5-6 membered unsaturated heterocyclic, such as furyl, pyrrolyl, pyrazolyl, imidazolyl, thiazolyl, thienyl, pyridyl or pyrimidinyl; and bicyclic unsaturated heterocyclic, such as indolyl, isoindolyl, quinolyl, benzothiazolyl, chromanyl, benzofuranyl or phthalimino.

The alkyl, aryl, heterocyclic groups of $R^2$ can be optionally substituted with one or more substituents, wherein the substituents are the same or different, and include hydroxyl; $C_{1-6}$ alkoxy, such as methoxy, ethoxy or propoxy; carboxyl; $C_{2-7}$ alkoxycarbonyl, such as methoxycarbonyl, ethoxycarbonyl or propoxycarbonyl) and halogen.

The alkyl, aryl, heterocyclic groups of $R^c$ can be optionally substituted with one or more substituents, wherein the substituents are the same or different, and include $C_{3-6}$ cycloalkyl; hydroxyl; $C_{1-6}$ alkoxy; amino; cyano; aryl; substituted aryl, such as 4-hydroxyphenyl, 4-methoxyphenyl, 4-chlorophenyl or 3,4-dichlorophenyl; nitro and halogen.

The heterocyclic ring formed together with $R^c$ and $R^1$ and the nitrogen atom to which they are attached can be optionally substituted with one or more substituents, wherein the substituents are the same or different, and include $C_{1-6}$ alkyl; hydroxy $C_{1-6}$ alkylene; $C_{1-6}$ alkoxy $C_{1-6}$ alkylene; hydroxyl; $C_{1-6}$ alkoxy; and cyano.

The term "amino acid" as used herein, comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, -methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an -methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "toll-like receptor" (TLR) refers to a member of a family of receptors that bind to pathogen associated molecular patterns (PAMPs) and facilitate an immune response in a mammal. Ten mammalian TLRs are known, e.g., TLR1-10.

The term "toll-like receptor agonist" (TLR agonist) refers to a molecule that binds to a TLR and antagonizes the receptor. Synthetic TLR agonists are chemical compounds that are designed to bind to a TLR and activate the receptor. Exemplary novel TLR agonists provided herein include "TLR-7 agonist" "TLR-8 agonist" and "TLR-9 agonist."

The term "nucleic acid" as used herein, refers to DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 7-position purine modifications, 8-position purine modifications, 9-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

A specific value for $X^1$ is a sulfur atom, an oxygen atom or —$NR^c$—.

Another specific $X^1$ is a sulfur atom.
Another specific $X^1$ is an oxygen atom.
Another specific $X^1$ is —$NR^c$—.
Another specific $X^1$ is —NH—.
A specific value for $R^c$ is hydrogen, $C_{1-4}$ alkyl or substituted $C_{1-4}$ alkyl.

A specific value for $R^1$ and $R^c$ taken together is when they form a heterocyclic ring or a substituted heterocyclic ring.

Another specific value for $R^1$ and $R^c$ taken together is substituted or unsubstituted morpholino, piperidino, pyrrolidino, or piperazino ring.

A specific value for $R^1$ is hydrogen, $C_{1-4}$alkyl, or substituted $C_{1-4}$alkyl.

Another specific $R^1$ is 2-hydroxyethyl, 3-hydroxypropyl, 4-hydroxybutyl, 2-aminoethyl, 3-aminopropyl, 4-aminobutyl, methoxymethyl, 2-methoxyethyl, 3-methoxypropyl, ethoxymethyl, 2-ethoxyethyl, methylthiomethyl, 2-methylthioethyl, 3-methylthiopropyl, 2-fluoroethyl, 3-fluoropropyl, 2,2,2-trifluoroethyl, cyanomethyl, 2-cyanoethyl, 3-cyanopropyl, methoxycarbonylmethyl, 2-methoxycarbonylethyl, 3-methoxycarbonylpropyl, benzyl, phenethyl, 4-pyridylmethyl, cyclohexylmethyl, 2-thienylmethyl, 4-methoxyphenylmethyl, 4-hydroxyphenylmethyl, 4-fluorophenylmethyl, or 4-chlorophenylmethyl.

Another specific $R^1$ is hydrogen, $CH_3$—, $CH_3$—$CH_2$—, $CH_3CH_2CH_2$—, hydroxy$C_{1-4}$alkylene, or $C_{1-4}$alkoxy$C_{1-4}$alkylene.

Another specific value for $R^1$ is hydrogen, $CH_3$—, $CH_3$—$CH_2$—, $CH_3$—O—$CH_2CH_2$— or $CH_3$—$CH_2$—O—$CH_2CH_2$—.

A specific value for $R^2$ is hydrogen, halogen, or $C_{1-4}$alkyl.

Another specific value for $R^2$ is hydrogen, chloro, bromo, $CH_3$—, or $CH_3$—$CH_2$—.

Specific substituents for substitution on the alkyl, aryl or heterocyclic groups are hydroxy, $C_{1-6}$alkyl, hydroxy $C_{1-6}$alkylene, $C_{1-6}$alkoxy, $C_{1-6}$alkoxy$C_{1-6}$alkylene, $C_{3-6}$cycloalkyl, amino, cyano, halogen, or aryl.

A specific value for $X^2$ is a bond or a chain having up to about 24 atoms; wherein the atoms are selected from the group consisting of carbon, nitrogen, sulfur, non-peroxide oxygen, and phosphorus.

Another specific value for $X^2$ is a bond or a chain having from about 4 to about 12 atoms.

Another specific value for $X^2$ is a bond or a chain having from about 6 to about 9 atoms.

Another specific value for $X^2$ is

Another specific value for $X^2$ is

A specific auxiliary group is an amino acid, a carbohydrate, a peptide, an antigen, a nucleic acid, a body substance, or a microbe.

A specific peptide, has from 2 to about 20 amino acid residues.

Another specific peptide, has from 10 to about 20 amino acid residues.

A specific auxiliary group is a carbohydrate.

A specific nucleic acid is DNA, RNA or PNA.

A specific body substance is a cell, lipid, vitamin, or co-factor.

Another specific body substance is a cell or lipid.

A specific antigen is a microbe.

A specific microbe is a virus, bacteria, or fungi.

Another specific microbe is a virus or a bacteria.

Specific bacteria are *Bacillus anthracis* (anthrax), *Listeria monocytogenes, Francisella tularensis*, or *Salmonella*.

Specific *Salmonella* are *typhimurium* or *enteritidis*.

Specific viruses are RNA viruses, a product of the RNA virus, or a DNA virus.

A specific DNA virus is the Hepatitis B virus.

Specific compounds of the invention have the general formula

IA-L-$A^1$;

IA-L-$(A^1)_2$;

IA-L-$A^1$-$A^1$;

IA-L-$A^1$-L-$A^1$;

$(IA)_2$-L-$A^1$-$A^1$;

$(IA)_2$-L-$A^1$-L-$A^1$;

$(IA)_2$-L-$A^1$; or $(IA)_2$-L-$(A^1)_2$;

wherein IA is as disclosed herein; L is absent or is a linking group; and each $A^1$ group independently represents an auxiliary group.

In one embodiment, the viral infection is caused by a coronavirus that causes Severe Acute Respiratory Syndrome (SARS), a Hepatitis B virus, or a Hepatitis C Virus.

In another embodiment, the viral infection is caused by a coronavirus that causes Severe Acute Respiratory Syndrome (SARS), a Hepatitis B virus, or a Hepatitis C Virus.

Specific cancers that can be treated include melanoma, superficial bladder cancer, actinic keratoses, intraepithelial neoplasia, and basal cell skin carcinoma, squamous, and the like. In addition, the method of the invention includes treatment for a precancerous condition such as, for example, actinic keratoses or intraepithelial neoplasia, familial polyposis (polyps), cervical dysplasia, cervical cancers, superficial bladder cancer, and any other cancers associated with infection (e.g., lymphoma Karposi's sarcoma, or leukemia); and the like.

Non limiting examples of the pathological conditions or symptoms that can be treated include viral diseases, cancer, inflammatory diseases of the gastrointestinal tract, brain, skin, joints, and other tissues.

The auxiliary groups are believed to enhance the drug activity of the pharmacophore (compounds of formula (I)) by (a) helping to direct the pharmacophore to the receptor within the endosomes of target cells; (b) by enhancing signal transduction induced by the pharmacophore, by cross-linking the receptor; and/or (c) the pharmacophore can enhance the response to the auxiliary group (e.g., immune response). The auxiliary groups should form generally stable bonds with the pharmacophore, and do not act as prodrugs.

The invention includes compositions of a compound of formula (I) optionally in combination with an inhibitor of inosine monophosphate dehydrogenase (IMPDH), an enantiomer of such a compound, a prodrug of such a compound, or a pharmaceutically acceptable salt of such a compound. As used herein an "IMPDH inhibitor" refers to an inhibitor of the enzyme inosine monophosphate dehydrogenase. Currently, three IMPDH inhibitors are used clinically: ribavirin, mizoribine, and mycophenolate mofetil. Ribavirin and mizoribine are prodrugs that are phosphorylated intracellularly to produce IMP analogs (Goldstein et al., Cuff Med Chem, 6:519-536 (1999)). Viramidine is a prodrug of Ribavirin. Mycophenolate mofetil is immunosuppressive, and has gastrointestinal irritative properties that may be attributable to its enterohepatic recirculation (Papageorgiou C, Mini Rev Med Chem., 1:71-77 (2001)). Mizoribine aglycone, a prodrug, is used as an IMPDH inhibitor. Other non-limiting examples IMPDH inhibitors, including prodrugs of mizoribine and mizoribine aglycone are known and are disclosed in published U.S. Patent application No. 20050004144.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds (conjugates) of the invention can be prepared using standard synthetic methods known in the art. A general ester synthesis is illustrated below:

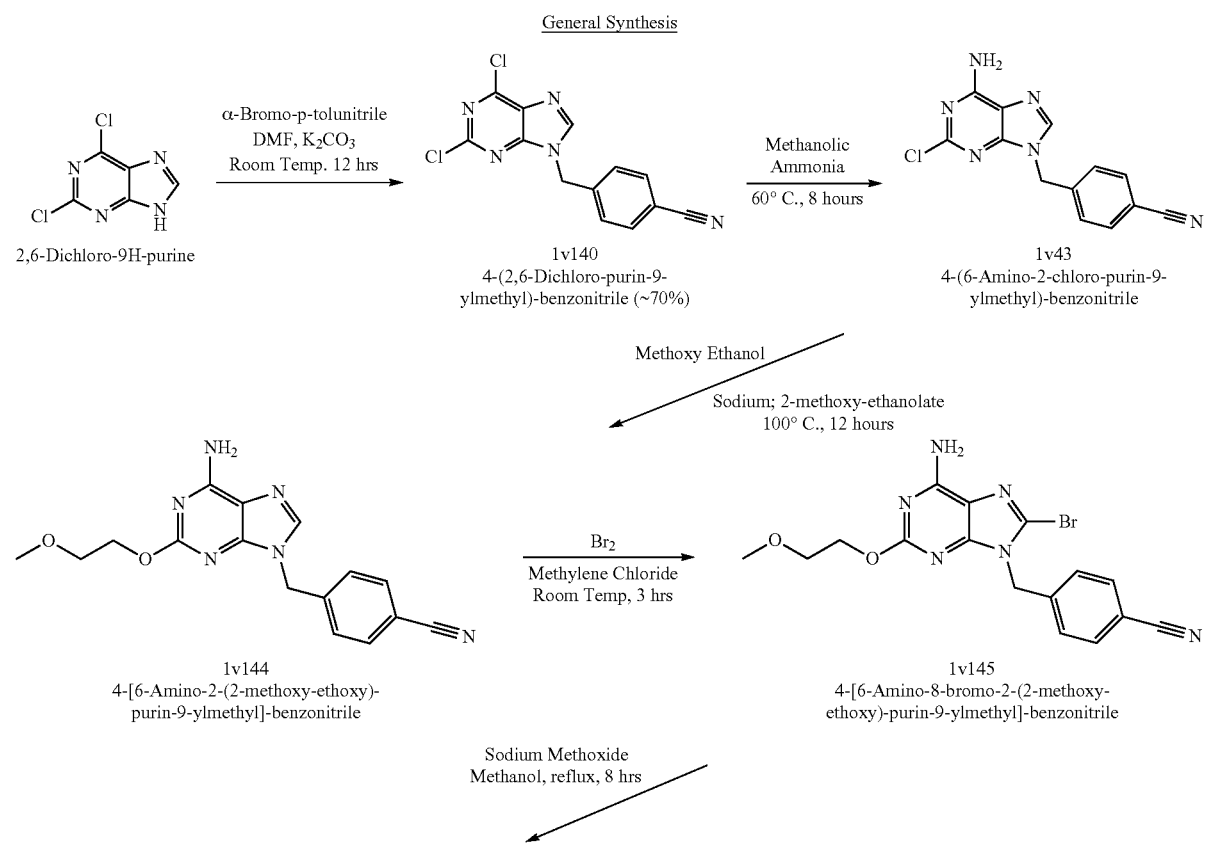

-continued
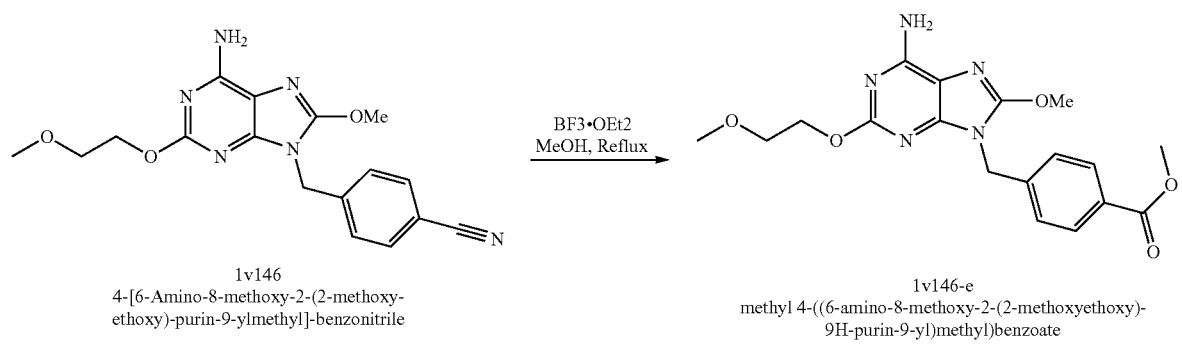
NHS Ester Synthesis
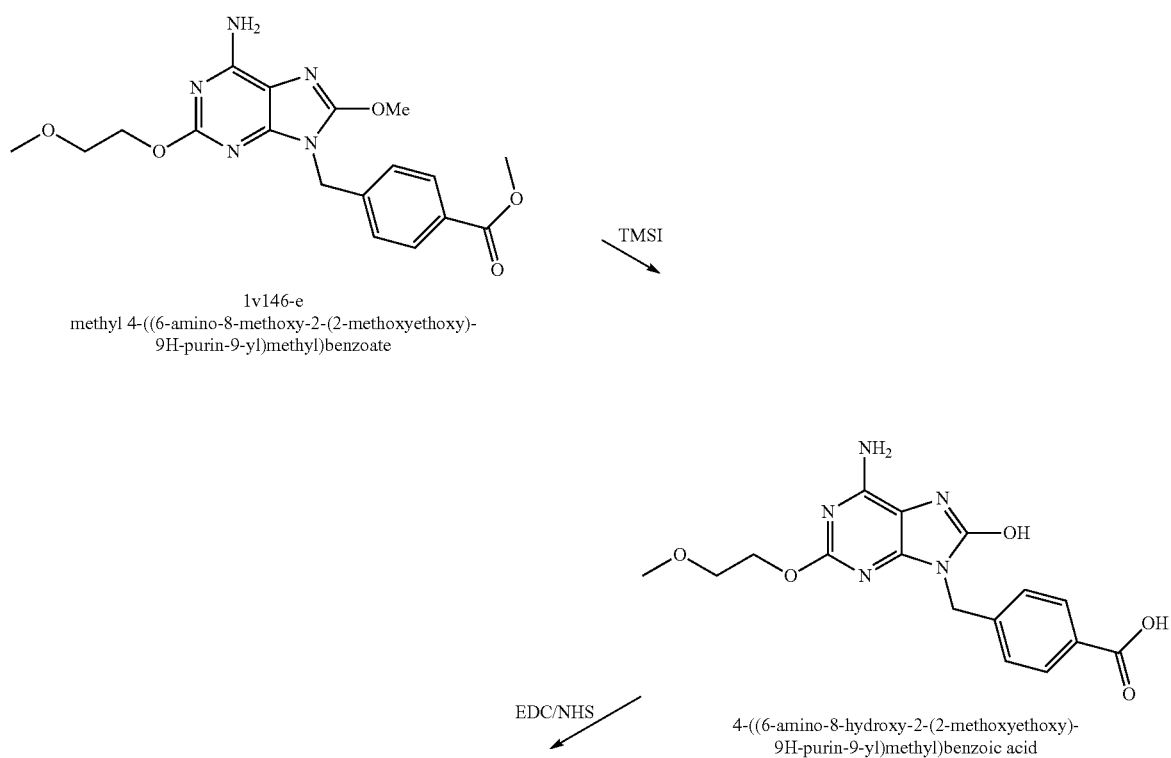
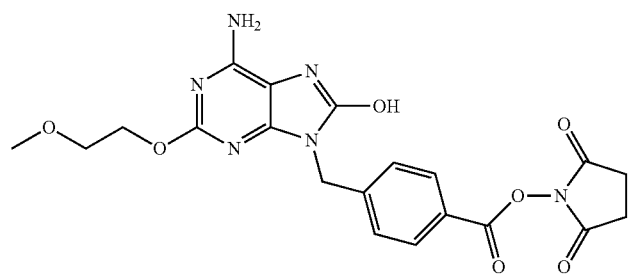

-continued
Aldehyde Synthesis

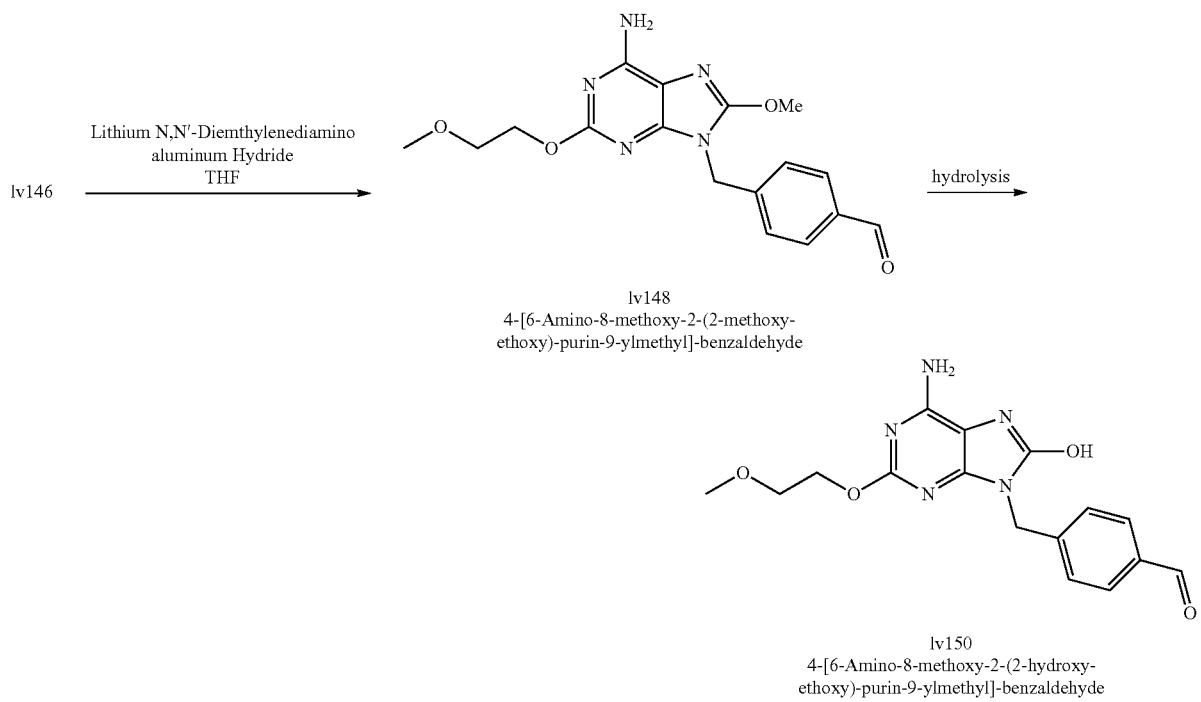

lv148
4-[6-Amino-8-methoxy-2-(2-methoxy-ethoxy)-purin-9-ylmethyl]-benzaldehyde lv150
4-[6-Amino-8-methoxy-2-(2-hydroxy-ethoxy)-purin-9-ylmethyl]-benzaldehyde Additional examples for preparing specific compounds are included herein.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to act as a TLR agonist may be determined using pharmacological models which are well known to the art, including the procedures disclosed by Lee et al.; PNAS, 100 p 6646-6651, 2003.

Processes for preparing compounds of formula (I) are provided as further embodiments of the invention and are illustrated by the following procedures in which the meanings of the generic radicals are as given above unless otherwise qualified.

EXAMPLES

General Chemistry.

Reagents and solvents were acquired from Aldrich, Milwaukee, Wis. Uncorrected melting points were determined on a Laboratory Device Mel-Temp II capillary melting point apparatus. Proton nuclear magnetic resonance spectra were recorded on a Varian Unity 500 NMR spectrophotometer at 499.8 MHz or on a Varian Mercury NMR spectrophotometer at 400.06 MHz. The chemical shifts were reported in ppm on the scale from the indicated reference. Positive and negative ion loop mass spectra were performed by Department of Chemistry UCSD, San Diego, Calif. Elemental analyses were performed by NuMega Resonance Labs, San Diego, Calif. Column chromatography was conducted on E Merck silica gel (230-400 mesh) with the indicated solvent system. Analytical thin layer chromatography (TLC) was conducted on silica gel 60 F-254 plates (EM Reagents).

Example 1

Preparation of
4-(2,6-dichloropurin-9-ylmethyl)benzonitrile 2,6-dichloro-9H-purine (16 mmol) is dissolved in DMF (50 mL) and potassium carbonate (50 mmol) is added. $\alpha$-Bromo-p-tolunitrile (22 mmol) is then added and the mixture is stirred at ambient temperature for 16 h. After filtration to remove insoluble inorganic salts, the filtrate is poured into water (1500 mL) and extracted with ethyl acetate (2×400 mL), dried over magnesium sulfate and evaporated to yield a residue which is subjected to flash silica gel chromatography using 1:2:10 ethyl acetate/acetone/hexanes. Yield 3.33 g (69%). UV, NMR and MS were consistent with structure assignment.

Example 2

Preparation of 4-(6-amino-2-chloropurin-9-ylmethylbenzonitrile

The product of example 1 (1.9 g) is placed in a steel reaction vessel and methanolic ammonia (80 mL, 7 N) is added. The sealed vessel is heated at 60° C. for 12 h, cooled in ice and the solid product filtered off. Yield 1.09 g. UV, NMR and MS were consistent with assigned structure.

Example 3

Preparation of 4-[6-amino-2-(2-methoxyethoxy)purin-9-ylmethyl]benzonitrile

Sodium salt of 2-methoxyethanol is generated by dissolving sodium metal (81 mg) in 2-methoxyethanol (30 mL) with heat. To this solution is added the product of example 2 (1.0 g) dissolved in methoxyethanol (300 mL, with heat). The reaction mixture is heated for 8 h at 115° C. bath temperature, concentrated in vacuo to near dryness and the residue partitioned between ethyl acetate and water. Flash silica gel chromatography of the organic layer using 5% methanol in dichloromethane gave 763 mg product. NMR is consistent with structure assignment.

Example 4

Preparation of 4-[6-amino-8-bromo-2-(2-methoxyethoxy)purin-9-ylmethyl]benzonitrile The product of example 3 (700 mg) is dissolved in dichloromethane (400 mL) and bromine (7 mL) is added dropwise. The mixture is stirred overnight at room temperature and extracted with aqueous sodium thiosulfate (2 L of 0.1 M) solution and then with aqueous sodium bicarbonate (500 mL, saturated). The residue from the organic layer is chromatographed on silica gel using 3% methanol in dichloromethane) to yield 460 mg of bromo product. NMR, UV and MS are consistent with structure assignment.

Example 5

Preparation of 4-[6-amino-8-methoxy-2-(2-methoxyethoxy)purin-9-ylmethyl]benzonitrile Sodium methoxide is generated by reaction of sodium metal (81 mg) in dry methanol (30 mL). The product of example 4 (700 mg) is dissolved in dry dimethoxyethane and the temperature raised to 100° C. After overnight reaction, the mixture is concentrated in vacuo and the residue is chromatographed on silica using 5% methanol in dichloromethane. Yield 120 mg. NMR is consistent with structure assignment.

Example 6

Preparation of Lithium N,N'-(dimethylethylenediamino)aluminum hydride

This reducing agent used to convert the nitrile to the aldehyde function is prepared essentially as described in *Bull.* *Korean Chem. Soc.* (2002), 23(12), 1697-1698. A 0.5 M solution in dry THF is prepared.

Example 7

Preparation of 4-[6-amino-8-methoxy-2-(2-methoxyethoxy)purin-9-ylmethyl]benzaldehyde The product of example 5 (100 mg) is dissolved in dry THF (3 mL) and cooled to 0° C. under argon. The reagent generated in example 6 (0.72 mL) is added to the reaction flask and the mixture is stirred at 0-5° C. for 1 h and then quenched by addition of 3 M HCl. The mixture is then extracted with ethyl acetate and then dichloromethane and concentrated in vacuo to yield 85 mg. NMR is consistent with structure assignment.

Example 8

Preparation of 4-[6-amino-8-hydroxy-2-(2-methoxyethoxy)purin-9-ylmethyl]benzaldehyde (1V150)

The product of example 7 (800 mg) is combined with sodium iodide (504 mg) and acetonitrile (40 mL), and then chlorotrimethylsilane (0.5 mL) is slowly added. The mixture is heated at 70° C. for 3.5 h, cooled and filtered. The solid product is washed with water, then ether to yield 406 mg. NMR, UV, MS are consistent with structure assignment. This material is suitable for conjugation reactions between linkers and auxiliary groups.

Example 9

Preparation of methyl 4-[6-amino-8-methoxy-2-(2-methoxyethoxy)purin-9-ylmethyl]benzoate. (Procedure as Described by Jayachitra, et al., *Synth. Comm.*, (2003) 33(19), 3461-3466.)

The product of example 5 (1 mmol) is dissolved in dry methanol (5 mL) and freshly distilled $BF_3$ etherate (4 mmol) is added to the solution. The resulting mixture is refluxed under argon for 20 h. The solvent is removed in vacuo and the residue is taken up in dichloromethane (10 mL) and extracted with dilute aqueous sodium bicarbonate (2×10 mL) and the organic layer is dried over magnesium sulfate. After evaporation the product is purified by silica gel column chromatography using 5% methanol in dichloromethane to yield 0.8 mmol.

Example 10

Preparation of 4-[6-amino-8-hydroxy-2-(2-methoxyethoxy)purin-9-ylmethyl]benzoic acid The product of example 9 (100 mg) is combined with sodium iodide (63 mg) and acetonitrile (10 mL), and then chlorotrimethylsilane (120 mL) is slowly added. The mixture is heated at 70° C. for 6 h, cooled and filtered. The solid product is washed with water, then ether to yield 51 mg.

Example 11

Preparation of 2,5-dioxopyrrolidin-1-yl 4-[6-amino-8-hydroxy-2-(2-methoxyethoxy)purin-9-ylmethyl]benzoate The product of example 10 (2 mmol) is dissolved in dichloromethane or dioxane (10 mL) and EDC (2 mmol) is added.

To this solution is added N-hydroxysuccinimide (2 mmol) and resulting mixture is stirred at room temperature for 1 h. The mixture is taken to dryness in vacuo and the crude product is purified by silica gel chromatography to yield 2 mmol of product that is suitable for conjugation reactions involving primary amines.

Example 12

Conjugation of 1V150 to Mouse Serum Albumin (MSA)

Modification of MSA with SANH: 200 µl of MSA (25 mg/ml) was mixed with 100 µl of conjugation buffer (1M NaPi, pH=7.2) and 690 µl of PBS. 844 µg of SANH in 10 µl of DFM (40-fold molar excess to MSA) was added to protein solution (Final concentration of MSA in reaction mixture is 5 mg/ml). After gentle mixing reaction was proceeded at room temperature for 2 hr. To remove excess of SANH the reaction mixture was loaded on NAP-10 column equilibrated with PBS and modified MSA was eluted with 1.5 ml of PBS.

Attachment of IV150 to MSA modified with SANH: 460 µg of IV150 dissolved in 10 µl of DMF was added to MSA modified with SANH and the reaction mixture was incubated at RT overnight. To remove excess of IV150 the reaction mixture was firstly concentrated to 1 ml using micro-spin column (Millipore: BIOMAX 5K) and loaded on NAP-10 column as mentioned above.

The abbreviations used herein have their conventional meaning within the chemical and biological arts. All publications, patents, and patent documents cited in the specification are incorporated by reference herein, as though individually incorporated by reference. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

What is claimed is:

1. A compound having formula (IA) and $R^3$:

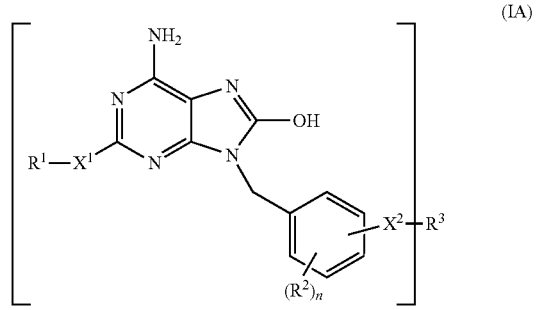

wherein $X^1$ is —O;
$R^1$ is $(C_1\text{-}C_{10})$alkyl or substituted $(C_1\text{-}C_{10})$alkyl, wherein the substituents are hydroxy, $C_{1-6}$alkyl, hydroxy $C_{1-6}$alkylene, or $C_{1-6}$alkoxy;
wherein n=4 and each $R^2$ is —H;
$X^2$ is a bond or a linking group having up to about 24 atoms; wherein the atoms in the chain of the linking group are selected from the group consisting of carbon, nitrogen, sulfur, non-peroxide oxygen, and phosphorous; and $R^3$ is a protein that directs formula (IA) to receptors within endosomes of target cells;
or a pharmaceutically acceptable salt of the compound,
wherein the ratio of the compound having formula (IA) to $R^3$ is 5:1.

2. The compound of claim 1, wherein $R^1$ is $C_{1-4}$alkyl, or substituted $C_{1-4}$alkyl.

3. The compound of claim 2, wherein $R^1$ is $CH_3$—, $CH_3$—$C_2$—, $CH_3CH_2CH_2$—, hydroxy$C_{1-4}$alkylene, or $C_{1-4}$alkoxy$C_{1-4}$alkylene.

4. The compound of claim 3, wherein $R^1$ is $CH_3$—, $CH_3$—$CH_2$—, $CH_3$—O—$CH_2CH_2$— or $CH_3$—$CH_2$—O—$CH_2CH_2$—.

5. The compound of claim 1, wherein $X^2$ is a bond or a chain having from about 4 to about 12 atoms.

6. The compound of claim 1, wherein $X^2$ is a bond or a chain having from about 6 to about 9 atoms.

7. The compound of claim 1, wherein $X^2$ is

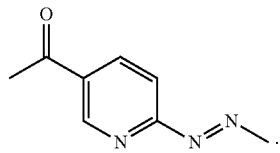

8. The compound of claim 1, wherein the protein is albumin.

9. The compound of claim 1, wherein the protein is ovalbumin.

10. A compound having formula (IA) and $R^3$:

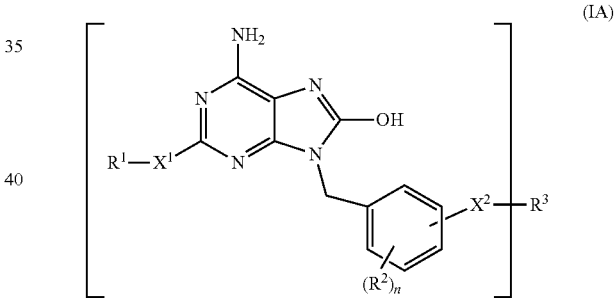

wherein $X^1$ is —O—;
$R^1$ is $(C_1\text{-}C_{10})$alkyl or substituted $(C_1\text{-}C_{10})$alkyl, wherein the substituents are hydroxy, $C_{1-6}$alkyl, hydroxy $C_{1-6}$alkylene, or $C_{1-6}$alkoxy;
each $R^2$ is —H and n=4;
$X^2$ is a bond or a linking group having up to about 24 atoms; wherein the atoms in the chain of the linking group are selected from the group consisting of carbon, nitrogen, sulfur, and non-peroxide oxygen; and $R^3$ is a protein that directs formula (IA) to receptors within endosomes of target cells;
or a pharmaceutically acceptable salt of the compound,
wherein the ratio of the compound having formula (IA) to $R^3$ is 5:1.

11. A pharmaceutical composition comprising the compound of claim 10, and a pharmaceutically acceptable carrier.

12. The compound of claim 10, wherein the protein is albumin.

13. The compound of claim 10, wherein the protein is ovalbumin.

* * * * *

UNITED STATES PATENT AND TRADEMARK OFFICE
CERTIFICATE OF CORRECTION

PATENT NO. : 9,359,360 B2  
APPLICATION NO. : 13/682208  
DATED : June 7, 2016  
INVENTOR(S) : Carson et al.

Page 1 of 1

It is certified that error appears in the above-identified patent and that said Letters Patent is hereby corrected as shown below:

On the Title Page

On page 3, in Column 1, item (56), under "Other Publications", Line 51, delete "Jul." and insert --Jun.--, therefor On page 4, in Column 2, item (56), under "Other Publications", Line 24, delete "Applicaiton" and insert --Application--, therefor On page 5, in Column 1, item (56), under "Other Publications", Line 4, delete ""Tumour" and insert --"Tumor--, therefor In the Specification In Column 1, Line 18, delete "The" and insert --This--, therefor In the Claims In Column 22, Line 6-7, in Claim 3, delete "$CH_3-C_2-$," and insert --$CH_3-CH_2-$,--, therefor Signed and Sealed this  
Fourteenth Day of April, 2020

Andrei Iancu  
*Director of the United States Patent and Trademark Office*